(12) United States Patent
Hickey et al.

(10) Patent No.: US 10,617,765 B2
(45) Date of Patent: Apr. 14, 2020

(54) ADDITIVE SYSTEMS FOR USE IN PROTEIN PEGYLATION

(71) Applicant: BRISTOL-MYERS SQUIBB COMPANY, Princeton, NJ (US)

(72) Inventors: Matthew R. Hickey, Yardley, PA (US); Antonio Ramirez, Princeton, NJ (US)

(73) Assignee: BRISTOL-MYERS SQUIBB COMPANY, Princeton, NJ (US)

(*) Notice: Subject to any disclaimer, the term of this patent is extended or adjusted under 35 U.S.C. 154(b) by 0 days.

(21) Appl. No.: 15/776,923

(22) PCT Filed: Nov. 22, 2016

(86) PCT No.: PCT/US2016/063313
§ 371 (c)(1),
(2) Date: May 17, 2018

(87) PCT Pub. No.: WO2017/091568
PCT Pub. Date: Jun. 1, 2017

(65) Prior Publication Data
US 2019/0351065 A1 Nov. 21, 2019

Related U.S. Application Data

(60) Provisional application No. 62/258,644, filed on Nov. 23, 2015.

(51) Int. Cl.
C07K 1/107 (2006.01)
A61K 47/60 (2017.01)
C07K 14/50 (2006.01)
C07K 14/64 (2006.01)

(52) U.S. Cl.
CPC ............ A61K 47/60 (2017.08); C07K 1/1077 (2013.01); C07K 14/50 (2013.01); C07K 14/64 (2013.01)

(58) Field of Classification Search
None
See application file for complete search history.

(56) References Cited

U.S. PATENT DOCUMENTS 7,468,458 B2 12/2008 Tian et al.

FOREIGN PATENT DOCUMENTS

WO WO2007056448 A2 5/2007

OTHER PUBLICATIONS

Abuchowski, A. et al., Alteration of Immunological Properties of Bovine Serum Albumin by Covalent Attachment of Polyethylene Glycol, J. Biol.Chem., 252:3578-3581 (1977).
Abuchowski, A. et al., Effect of Covalent Attachment of Polyethylene Glycol on Immunogenicity and Circulating Life of Bovine Liver Catalase, J. Biol. Chem., 252:3582-3586 (1977).
Bhide, S.V. et al., Mutagenicity and Carcinogenicity of Mono- and Diacetyl Hydrazine, 20 Cancer Lett., 23:235 (1984).
Crisalli, P. et al., Water-Soluble Organocatalysts for Hydrazone and Oxime Formation, J. Org. Chem., 78:1184-1189 (2013).
Jencks, W.P., Mechanism and Catalysis of Simple Carbonyl Group Reactions, Prog. Phys. Org. Chem., 2:63-128 (1964).
Liu, C.C. et al., Adding New Chemistries to the Genetic Code, Annu. Rev. Biochem., 79:413-444 (2010).
Pubchem: "4-Aminobenzoic hydrazide 95%; SID=24890836", PubChem Substance Database, Apr. 14, 2009 (Apr. 14, 2009), XP055338675, URL:https://pubchem.ncbi.nlm.nih.gov/substance/24890836.
Roberts, M.J. et al., Chemistry for peptide and protein PEGylation, Adv. Drug Delivery Reviews, 54:459-476 (2002).
Harris, J. M. et al. in Poly(ethylene glycol) Chemistry: Biotechnical and Biomedical Applications, Synthesis of New Poly (Ethylene Glycol) Derivatives, Chapter 22, Harris, J.M., ed., Plenum Press, NY (1992).
Zalipsky et al. in Poly(ethylene glycol) Chemistry: Biotechnical and Biomedical Applications, Use of Functionalized Poly (Ethylene Glycol)s for Modification of Polypeptides, Chapter 21, Harris, J.M., ed., Plenum Press, NY (1992).

*Primary Examiner* — Fred H Reynolds

(57) ABSTRACT

The present disclosure provides an additive system for use in protein PEGylation. The additive system includes p-aminobenzoic hydrazide used either alone or in combination with aromatic amines, such as 3,5-diaminobenzoic acid, or with ammonium salts such as ammonium chloride or ammonium acetate. The disclosed additive combination provides several benefits including increased reaction rates, higher yields and reduction in the aminoxy-PEG equivalents required to complete the conjugation reaction. Typical reactions can be run by combining the additive or additive system with a solution of a protein and aminoxy-PEG reagent. The solution is adjusted to pH 4 and held at 20-25° C. without stirring until completion, typically within 24 hours.

8 Claims, 27 Drawing Sheets

General Mechanism for the Formation of Ketoximes

Model reaction for the screening of additives. Reaction Conditions: 1 (3.6 mmol) and 2 (3.6 mmol) in 1.0 mL Acetate Buffer (20 mM, pH 4.0) at Room Temperature (23°C).

Relative rates ($k_{rel}$) observed for different additives. Acetyl hydrazide ($k_{rel} \approx 2$) is shown in a box.
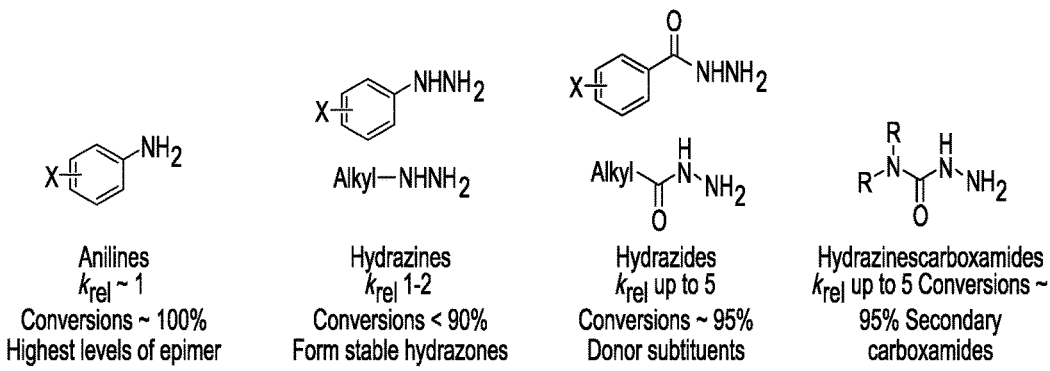
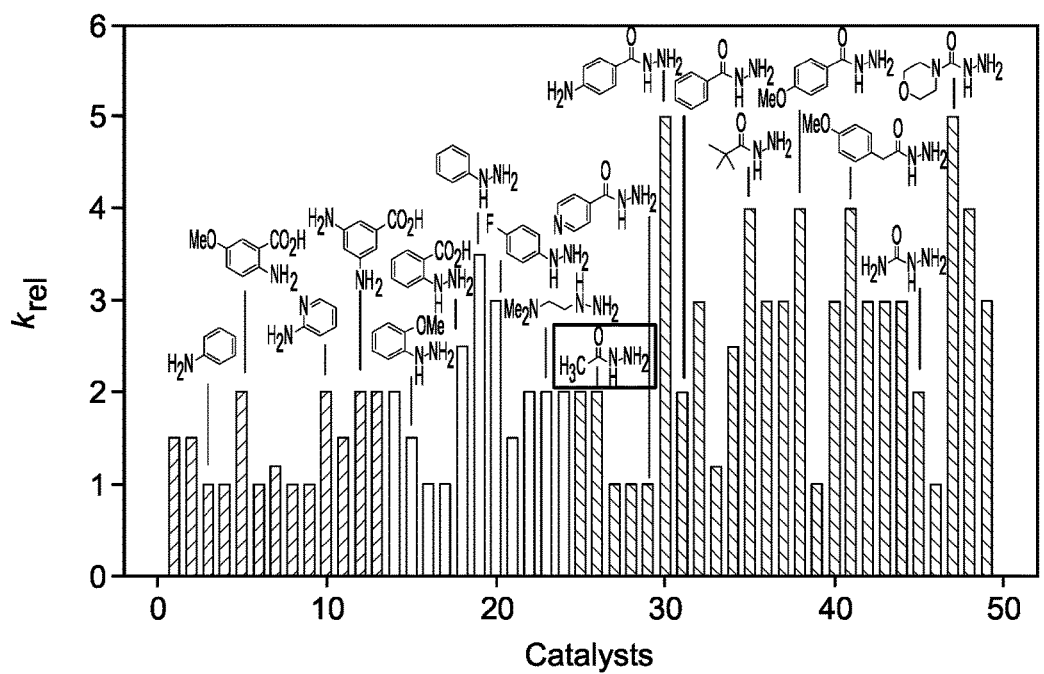
FIG. 6

Time course for the reaction of dipetide 1 with O-benzylhydroxylamine (2) in the presence of (a) 1 equiv pyrazoleamine (red); (b) 1 equiv MCH (blue); (c) 1 equiv pyrazoleamine and 1 equiv MCH (green). The reaction profile obtained in the absence of additives is shown in grey.

Aromatic region of the ¹H NMR spectra of samples containing dipeptide 1 (a) (blue); with (b) 1 equiv MCH (green); (c) 1 equiv MCH, and 1 equiv pyrazoleamine (grey); (d) 1 equiv pyrazoleamine (red). Synergistic effect between MCH and pyrazoleamine additives yields mixtures with higher concentration of active intermediates relative to samoles containing only one additive.

Left: PEGylation of the dipeptide 1 with 30 equiv PABH and 1.2 equiv 20 kDa PEG-OA; the hydrazone intermediate is tracked as the green points. Right: PEgylation reaction in which 1.2 equiv PEGylating reagent were added after equilibrating the dipeptide with 30 equiv PABH overnight.

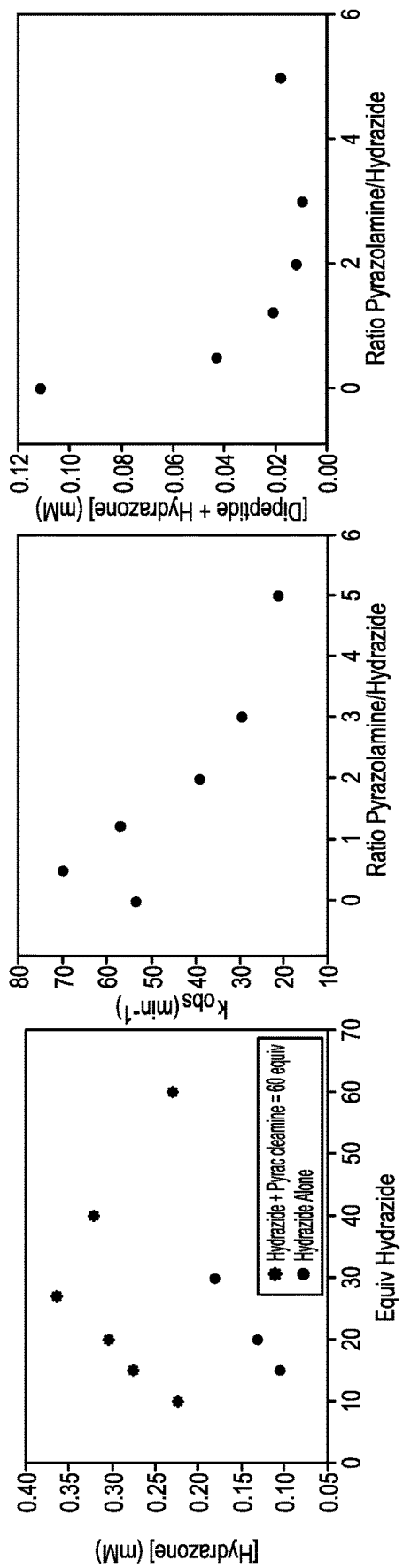

FIG. 10

Left: Plot of hydrazone concentration versus equivalents of PABH for the PEGylation of dipeptide 1; the blue points indicate the reaction mixture in which pyrazoleamine was omitted. Center: Effect of different combinations of PABH and pyrazoleamine on reaction rates. Right: Final concentration of dipeptide 1 and its hydrazone derivative in reaction mixtures containing PABH and pyrazoleamine.

Plot of remaining dipeptide 1 at the end of the reaction, versus total equivalents additive and pyrazoleamine: PABH ratio.

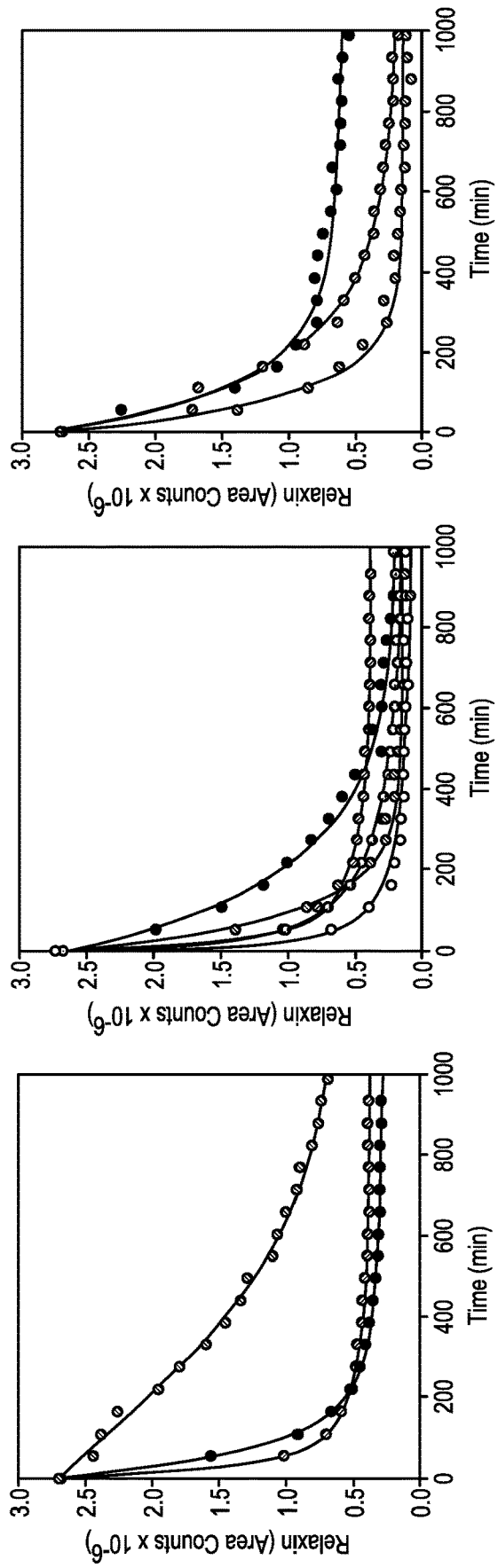

Left: Time course for the reaction of Relaxin with 20 kDa PEG-OA (1.5 equiv) in the presence of (a) 30 equiv acetyl hydrazide (blue); (b) 30 equiv MCH (red); the reaction profile obtained in the absence of additives is shown in grey color. Center: Time course for the reaction of Relaxin with PEG-OA (1.5 equiv) in the presence of (a) 30 equiv pyrazoleamine (blue); (b) 30 equiv MCH (red); (c) 10 equiv MCH (purple); (d) 30 equiv pyrazoleamine and 10 equiv MCH (green); (e) 30 equiv MCH and 30 equiv pyrazoleamine. Right: Time course for the reaction of Relaxin with PEG-OA (1.5 equiv) in the presence of 30 equiv pyrazoleamine and 10 equiv MCH at (a) 40 °C; (b) 10 °C; (c) 25 °C.

FIG. 12

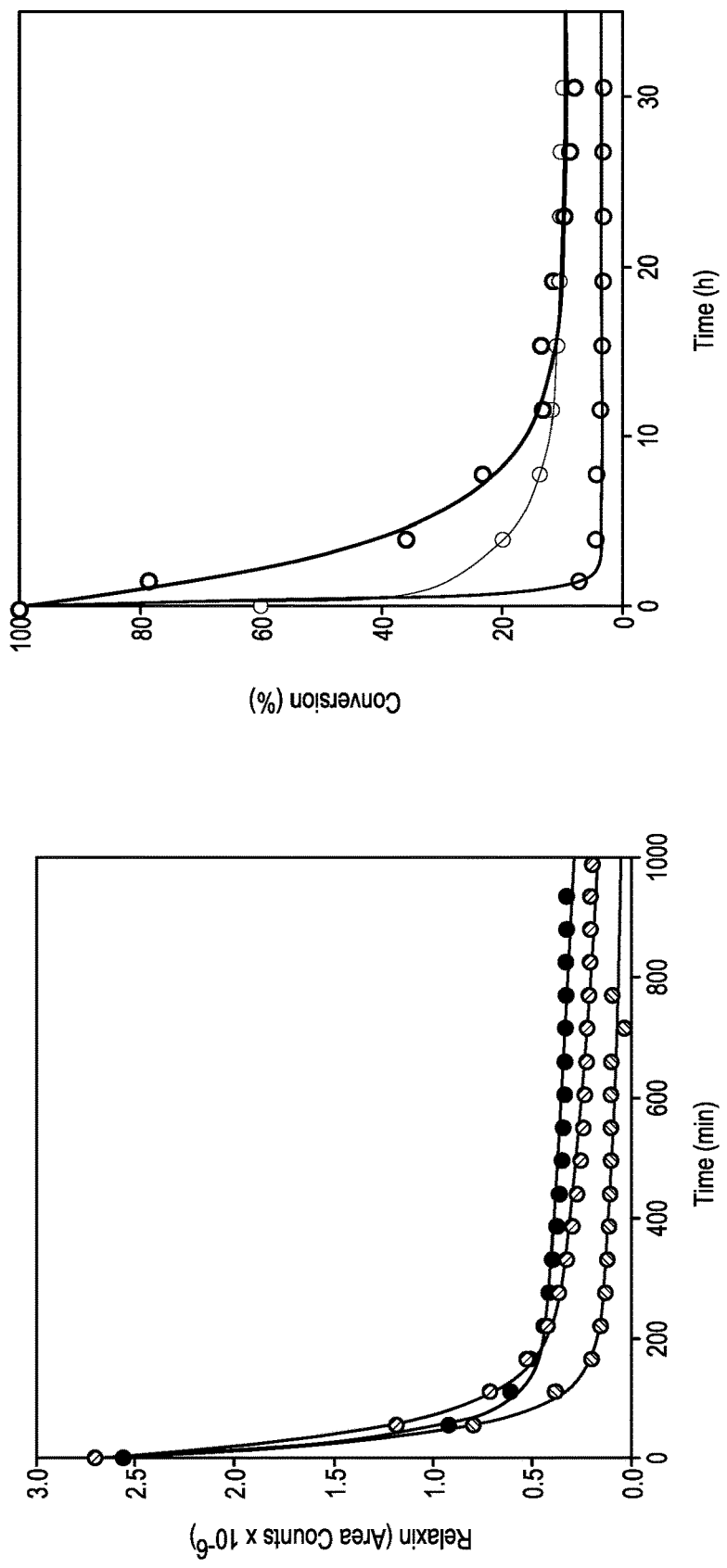

FIG. 13

Left: Time course for the reaction of Relaxin with 20 kDa PEG-OA (1.2 equiv) in the presence of (a) 30 equiv MPCH and 30 equiv pyrazoleamine (green); 30 equiv PH and 30 equiv pyrazoleamine (blue); and (c) 30 equiv MCH and 30 equiv pyrazoleamine in urea 6M (red). Right: Time course for the reaction of Relaxin with PEG-OA (1.2 equiv) in the presence of (a) 30 equiv PH and 60 equiv pyrazoleamine (blue); (b) 30 equiv acetyl hydrazide and 60 equiv pyrazoleamine (green); and (c) 30 equiv PABH and 60 equiv pyrazoleamine (red).

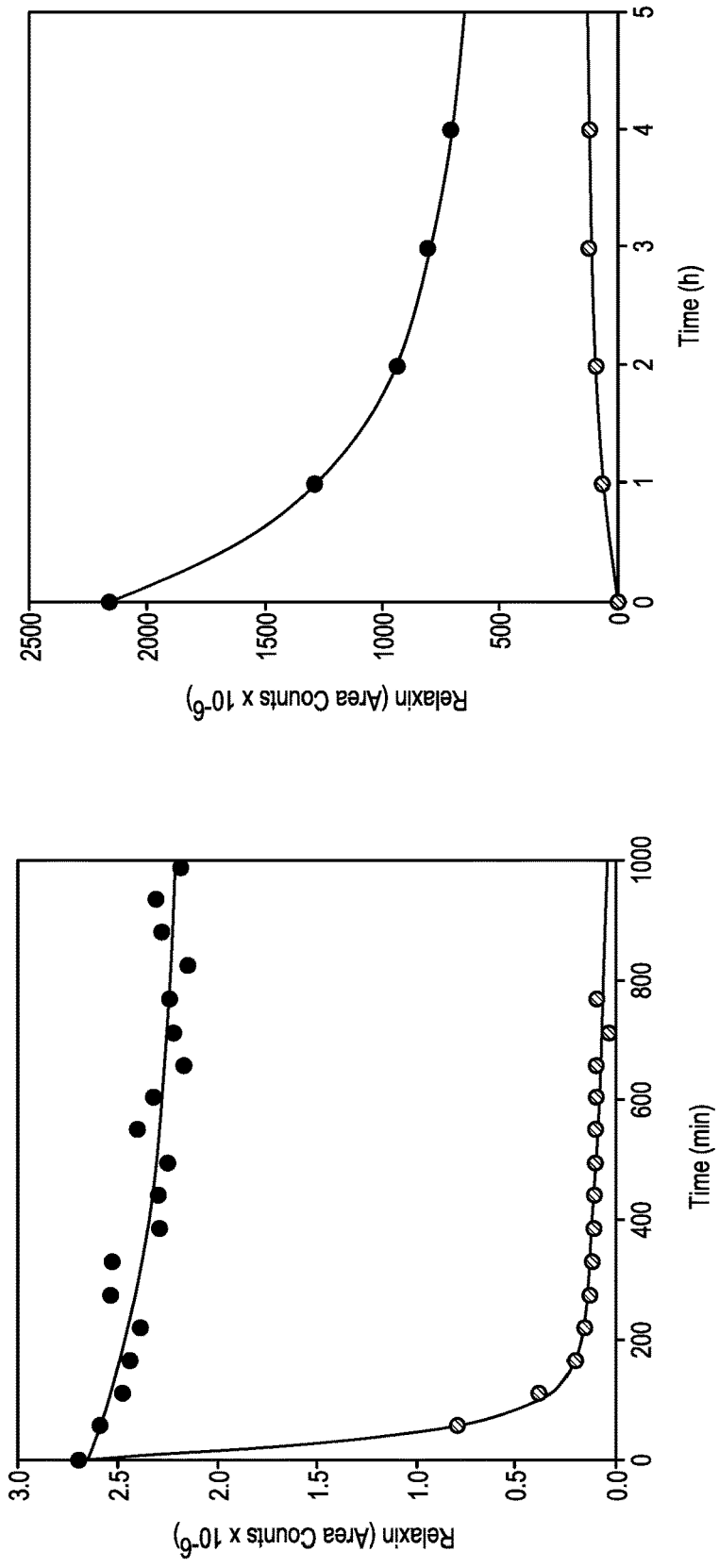

Left: Time course for the reaction of Relaxin with 20 kDa PEG-OA (1.2 equiv) in the presence of urea 6M with (a) 30 equiv MCH and 30 equiv pyrazoleamine (red); (b) 30 equiv MCH, 30 equiv pyrazoleamine, and 30 equiv $NH_2OH$ (blue). Right: Time course for the decay of Relaxin with PEG-OA (1.2 equiv) in the presence of urea 6M with 30 equiv MCH and 30 equiv pyrazoleamine (blue); the oxime peak (red) grows during the reaction, suggesting parallel formation of hydroxylamine from PEG-OA decomposition.

FIG. 15

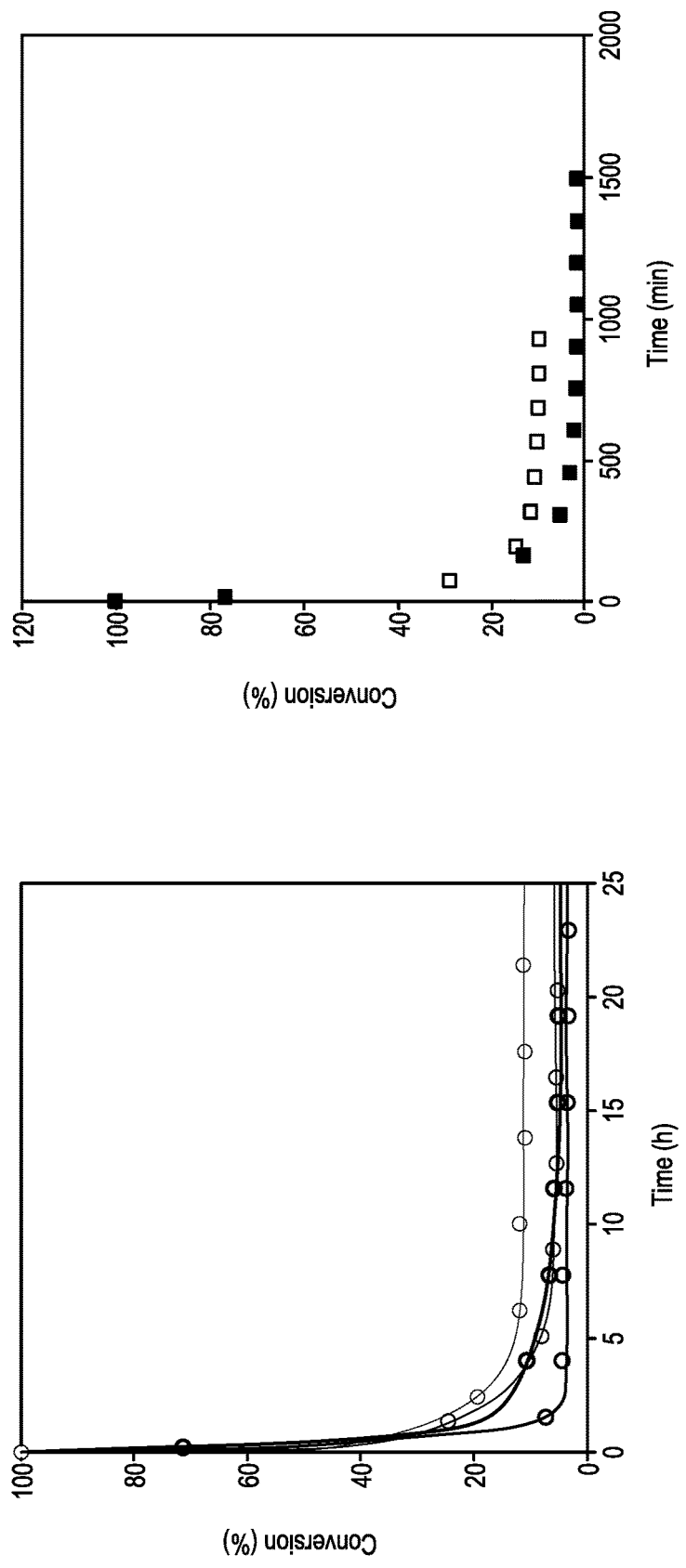

FIG. 16

Left: Time course for the reaction of Relaxin with 20 kDa PEG-OA (1.2 equiv) in the presence of 30 equiv PABH and (a) 60 equiv ethylenediamine (grey); (b) 60 equiv 3,5-diaminobenzoic acid (green); (c) 60 equiv m-phenylendiamine (blue); and 60 equiv pyrazoleamine (red). Right: Time course for the reaction of Relaxin with PEGOA (1.2 equiv) in the presence of (a) 30 equiv PABH and 60 equiv 3,5-diaminobenzoic acid (green); and (b) 60 equiv PABH and 120 equiv $NH_4Cl$ (blue).

PEgylation results for *o*- and *m*-phenylendiamine illustrating the curvature of the plot of total equiv versus amine: PABH ratio versus final FGF21 concentration. Left: *o*-phenylenediamine. Right: *m*-phyenylenediamine.

Plots of total additive equivalents versus amine: PABH ratio and conversion for PEGylations using PABH and 3,5-diaminobenzoic acid. Left: FGF21 with 30 kDa PEg-OA. Right: Relaxin with 20 kDa PEG-OA.

Left: Time course for the reaction of Relaxin with 20 kDa PEG-OA (1.2 equiv) in the presence of 120 equiv salt and 60 equiv PABH catalyst using (a) urea 6 M (green); $NH_4Cl$ (grey); and (c) $(NH_4)_2SO_4$ (purple).

Time course for the reaction of Relaxin with 20 kDa PEG-OA (1.2 equiv) in the absence of additives (blue) and the presence of: (a) 120 equiv $NH_4Cl$ (red), (b) 60 equiv acetyl hydrazide (grey); and (c) 60 equiv acetyl hydrazide and 120 equiv $NH_4Cl$ (green).

Left: UV spectra of Relaxin before and after the addition of 120 equiv NH4Cl (blue and red, respectively). Right: Amino acid sequence of Relaxin highlighting the aromatic resides in red.

Left: IR spectra of Relaxin before and after the addition of 120 equiv NH4Cl (blue and purple, respectively). Right: Inset of the IR spectrum after addition of 120 equiv NH4Cl with tentative assignments for the structural changes.

Near UV CD Spectra of Relaxin Before (Blue) and After the Addition of 120 Equiv NH4Cl (Blue and Green, Respectively)

Structures of Potential Impurities Present in Commercial PABH
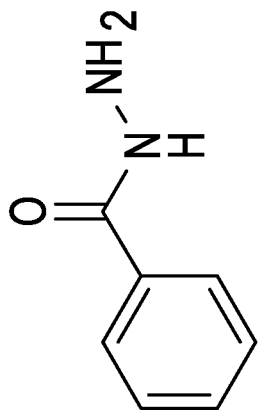
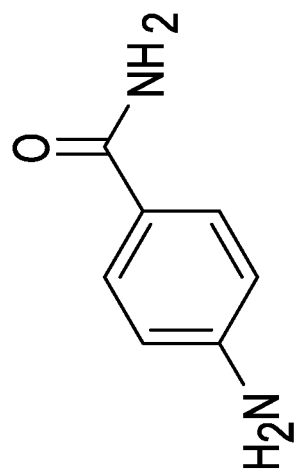
FIG. 27

ADDITIVE SYSTEMS FOR USE IN PROTEIN PEGYLATION

CROSS-REFERENCE TO RELATED APPLICATIONS

This patent application claims the benefit of provisional patent application 62/258,644, filed Nov. 23, 2015, the teachings of which are specifically incorporated by reference herein.

TECHNICAL FIELD

The present disclosure relates to an improved additive system for use in protein PEGylation reaction. In particular, the disclosure identifies an additive for the conjugation reaction between proteins containing the p-acetylphenylalanine residue and an aminoxy-PEG compound.

BACKGROUND

The PEGylation of proteins is a conjugation process that involves the attachment of a polyethylene glycol derivative to a therapeutic protein to improve its stability and pharmacokinetics by reducing clearance rates and providing a steric shield from proteolytic enzymes and immune system recognition (Roberts, M. J. et al., *Adv. Drug Delivery Rev,* 54:459 (2002)). In general, the PEGylation technologies can be classified into two types, namely random and site-specific conjugations. Random PEGylations arbitrarily link the PEGylating reagent to reactive amino acids such as lysine or cysteine to afford a mixture of PEGylated products. In contrast, site-specific conjugations exploit the unambiguous reactivity of a native functionality (e.g., the N- or C-terminal groups) or an unnatural amino acid (e.g., p-acetylphenyl-alanine-pAcF) to control the location and number of PEG residues attached to the protein. Site specific conjugation reaction involving ketoxime formation between a PEGylating reagent and a pAcF residue is incorporated in the substrate protein via expansion of the genetic code (Liu, C. C. et al., *Annu. Rev. Biochem.,* 79:413 (2010); Tian, F. et al., "Accelerants for the modification of non-natural amino acids and non-natural amino acid polypeptides", U.S. Pat. No. 7,468,458 (Dec. 23, 2008)). Despite their and demonstrated utility, conjugations based on the formation of ketoximes suffer from slow rates and incomplete conversions (Crisalli, P. et al., *J. Org. Chem.,* 78:1184 (2013)). Attempts to improve ketoxime formation include the use of excess PEGylating reagent, high temperatures, or high concentrations of toxic catalysts. These solutions, however, introduce additional steps to eliminate the excess PEGylating reagent or toxic catalyst from the product and often compromise the stability of the protein. Additionally, the old methods do not use additives, use a denaturant (urea), and/or use acetylhydrazide (AcNHNH2) as the additive. AcNHNH2 and related structures have been defined in PCT Publication No. WO 2007/056448.

What is now needed in the art are new methods to upgrade the yield and rates for the PEGylation of proteins (Relaxin and FGF21) containing a pAcF residue by examining the mechanistic principles that effect stalling and by identifying new additives that accelerate the reaction and promote high conversions at low PEG: protein molar ratios. The methods should be economical, promote higher conversions with considerably lower amounts of PEGylating reagent, promote faster reactions that circumvent the need for high reaction temperatures and elimination of genotoxic material.

SUMMARY

In a first embodiment, the present disclosure provides an improved additive system for protein PEGylation reaction, said system comprising p-aminobenzoic hydrazide alone or in combination with aromatic amines or ammonium salts.

In another embodiment, the present disclosure provides a process for obtaining PEGylated protein, said process comprising steps of: identifying a protein, PEG reagent and an additive system; and solubilizing the protein followed by combining with PEG reagent in presence of the additive system to obtain PEGylated protein with high yield.

In a further embodiment, the present disclosure provides a pharmaceutical composition comprising a PEGylated protein obtained by the process as mentioned in the above embodiment for use in therapy for a subject in need thereof.

BRIEF DESCRIPTION OF THE FIGURES

FIG. 6: Relative rates ($k_{rel}$) observed for different additives. Acetyl hydrazide ($k_{rel}$≈2) is shown in a box.

FIG. 10: Left: Plot of hydrazone concentration versus equivalents of PABH for the PEGylation of dipeptide 1; the blue points indicate the reaction mixture in which pyrazoleamine was omitted. Center: Effect of different combinations of PABH and pyrazoleamine on reaction rates. Right: Final concentration of dipeptide 1 and its hydrazone derivative in reaction mixtures containing PABH and pyrazoleamine.

FIG. 12: Left: Time course for the reaction of Relaxin with 20 kDa PEG-OA (1.5 equiv) in the presence of (a) 30 equiv acetyl hydrazide (blue); (b) 30 equiv MCH (red); the reaction profile obtained in the absence of additives is shown in grey color. Center: Time course for the reaction of Relaxin with PEG-OA (1.5 equiv) in the presence of (a) 30 equiv pyrazoleamine (blue); (b) 30 equiv MCH (red); (c) 10 equiv MCH (purple); (d) 30 equiv pyrazoleamine and 10 equiv MCH (green); (e) 30 equiv MCH and 30 equiv pyrazoleamine. Right: Time course for the reaction of Relaxin with PEG-OA (1.5 equiv) in the presence of 30 equiv pyrazoleamine and 10 equiv MCH at (a) 40° C.; (b) 10° C.; (c) 25° C.

FIG. 13: Left: Time course for the reaction of Relaxin with 20 kDa PEG-OA (1.2 equiv) in the presence of (a) 30 equiv MPCH and 30 equiv pyrazoleamine (green); (b) 30 equiv PH and 30 equiv pyrazoleamine (blue); and (c) 30 equiv MCH and 30 equiv pyrazoleamine in urea 6M (red). Right: Time course for the reaction of Relaxin with PEG-OA (1.2 equiv) in the presence of (a) 30 equiv PH and 60 equiv pyrazoleamine (blue); (b) 30 equiv acetyl hydrazide and 60 equiv pyrazoleamine (green); and (c) 30 equiv PABH and 60 equiv pyrazoleamine (red).

FIG. 15: Left: Time course for the reaction of Relaxin with 20 kDa PEG-OA (1.2 equiv) in the presence of urea 6M with (a) 30 equiv MCH and 30 equiv pyrazoleamine (red); (b) 30 equiv MCH, 30 equiv pyrazoleamine, and 30 equiv $NH_2OH$ (blue). Right: Time course for the decay of Relaxin with PEG-OA (1.2 equiv) in the presence of urea 6M with 30 equiv MCH and 30 equiv pyrazoleamine (blue); the oxime peak (red) grows during the reaction, suggesting parallel formation of hydroxylamine from PEG-OA decomposition.

FIG. 16: Left: Time course for the reaction of Relaxin with 20 kDa PEG-OA (1.2 equiv) in the presence of 30 equiv PABH and (a) 60 equiv ethylenediamine (grey); (b) 60 equiv 3,5-diaminobenzoic acid (green); (c) 60 equiv m-phenylenediamine (blue); and 60 equiv pyrazoleamine (red). Right: Time course for the reaction of Relaxin with PEGOA (1.2 equiv) in the presence of (a) 30 equiv PABH and 60 equiv 3,5-diaminobenzoic acid (green); and (b) 60 equiv PABH and 120 equiv $NH_4Cl$ (blue).

FIG. 27: Structures of potential impurities present in commercial PABH.

DETAILED DESCRIPTION

Figure 1:
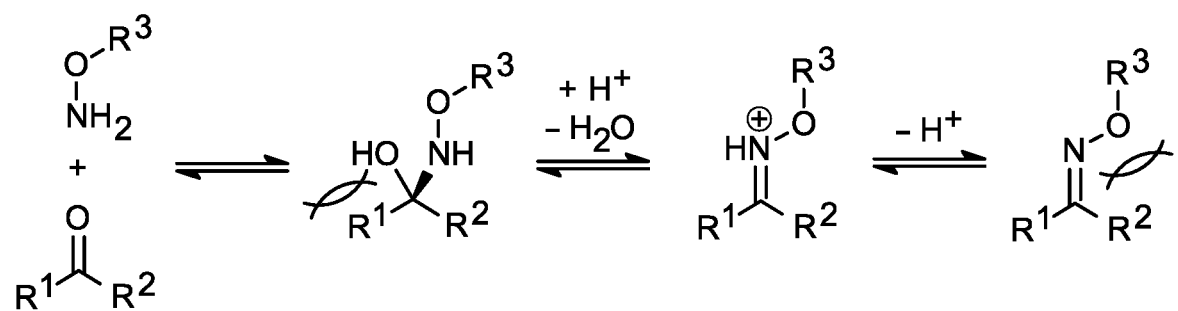
FIG. 1: General mechanism for the formation of ketoximes.

Unless otherwise specifically set forth elsewhere in the application, the following terms may be used herein, and shall have the following meanings.

Abbreviations

PEG: polyethylene glycol
PEG-OA: polyethylene glycol-oxyamine
mPEG: methoxy polyethylene glycol
MCH: morpholine 4-carbohydrazide
MPCH: 4-methylpiperazine-1-carbohydrazide
PH: Pivalic hydrazide
PABH: p-amino benzoic hydrazide
PMBH: p-methoxy benzoic hydrazide It must be noted that as used herein, the singular forms "a", "an", and "the" include plural referents unless the context clearly dictates otherwise. Unless defined otherwise, all technical and scientific terms used herein have the same meaning as commonly understood by one of ordinary skill in the art. Unless otherwise stated, all ranges described herein are inclusive of the specific endpoints. The following terms are provided below.

About: The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 5 percent up or down (higher or lower).

Additive system: The term "additive system" is used herein to mean "catalyst compound", either alone or in combination. For, e.g., p-aminobenzoic hydrazide alone or in combination with aromatic amines namely 3,5-diaminobenzoic acid, 0-phenylenediamine, 1-pyridin-2-yl-ethylamine, 2-(dimethylamino)ethylhydrazine, m-phenylenediamine and 2-picolylamine or ammonium salts namely ammonium acetate and ammonium chloride. Preferable catalyst compounds includes p-aminobenzoic hydrazide with 3,5-diaminobenzoic acid or p-aminobenzoic hydrazide with ammonium chloride.

Comprising: The term "comprising" means "including", e.g., a composition "comprising" X may consist exclusively of X or may include something additional, e.g., X+Y.

PEG: The term "PEG" when used in the context of this disclosure refers to polyethylene glycol or derivatized polyethylene glycol.

PEGylation or pegylation process: The term "PEGylation" or "pegylation process" refers to the process of attachment of polyethylene glycol (PEG) polymer chains to another molecule, in the context of the present disclosure, to proteins containing p-acetylphenylalanine (pAcF) residue including, but not limited to, Relaxin and FGF21.

Conjugation: The term "conjugation" as used herein refers to a conjugation reaction between proteins containing p-acetylphenylalanine residue and an aminoxy-PEG compound.

It generally involves the activation of PEG and coupling of the activated PEG-intermediates directly to target proteins/peptides or to a linker, which is subsequently activated and coupled to target proteins/peptides (see Abuchowski, A. et al., *J. Biol. Chem.*, 252:3571 (1977) and *J. Biol. Chem.*, 252:3582 (1977), Zalipsky et al. in *Poly(ethylene glycol) Chemistry: Biotechnical and Biomedical Applications*, Chapters 21 and 22, Harris, J. M., ed., Plenum Press, N.Y. (1992)). It is noted that a polypeptide containing a PEG molecule is also known as a conjugated or PEGylated protein, whereas the protein lacking an attached PEG molecule can be referred to as unconjugated or free.

PEG reagent or PEGylating reagent: Reagents that help in PEGylation reaction.

It will be understood that any given exemplary embodiment can be combined with one or more additional exemplary embodiments.

In a first aspect, the present disclosure provides an improved additive system for protein PEGylation reaction, said system comprising p-aminobenzoic hydrazide alone or in combination with aromatic amines or ammonium salts.

In a first embodiment of the first aspect, the aromatic amine is selected from a group consisting of 3,5-diaminobenzoic acid, O-phenylenediamine, 1-pyridin-2-yl-ethylamine, 2-(dimethyl amino) ethylhydrazine, m-phenylenediamine and 2-picolylamine.

In a second embodiment of the first aspect, the ammonium salt is selected from a group consisting of ammonium acetate and ammonium chloride.

In a third embodiment of the first aspect, the preferred system combination includes p-aminobenzoic hydrazide with 3,5-diaminobenzoic acid or p-Aminobenzoic hydrazide with ammonium chloride.

In a fourth embodiment of the first aspect, the reaction is a conjugation reaction between proteins containing the p-acetylphenylalanine reside and an aminoxy-PEG compound.

In a fifth embodiment of the first aspect, the additive system augments the conjugation reaction rates, provides high yield of the conjugated product and facilitates reduction in the aminoxy-PEG equivalents required to complete the conjugation reaction.

In a second aspect, the present disclosure provides a process for obtaining PEGylated protein, said process comprising steps of: identifying a protein, PEG reagent and an additive system; and solubilizing the protein followed by combining with PEG reagent in presence of the additive system to obtain PEGylated protein with high yield.

In a first embodiment of the second aspect, the protein is Relaxin or FGF21 containing a pAcF residue.

In a second embodiment of the second aspect, the solubilized protein solution combined with PEG reagent is maintained at a pH of about 4.

In a third embodiment of the second aspect, the reaction mixture is held at a temperature ranging from about 20° C. to about 25° C.

In a fourth embodiment of the second aspect, the additive system includes p-aminobenzoic hydrazide alone or in combination with combination with aromatic amines, such as 3,5-diaminobenzoic acid or ammonium salts such as ammonium acetate or ammonium chloride.

In a fifth embodiment of the second aspect, the additive combination of high quality p-aminobenzoic hydrazide with ammonium chloride is preferred for use at large scale production of PEGylated proteins.

In a sixth embodiment of the second aspect, the PEG reagents are selected from a group comprising PEG-OA and other PEG derivatives with aminoxy group.

In a third aspect, the present disclosure provides a pharmaceutical composition comprising a PEGylated protein obtained by the process of recited in the second aspect and its embodiments for use in therapy for a subject in need thereof.

EXAMPLES

The present disclosure will now be described in connection with certain embodiments which are not intended to limit its scope. On the contrary, the present disclosure covers all alternatives, modifications, and equivalents as can be included within the scope of the claims. Thus, the following Examples, which include specific embodiments, will illustrate one practice of the present disclosure, it being understood that the Examples are for the purposes of illustration of certain embodiments and are presented to provide what is believed to be the most useful and readily understood description of its procedures and conceptual aspects.

The general mechanism of the reaction between a carbonyl group and a hydroxylamine derivative is well-understood for small molecule reactants (Jencks, W. P., *Prog. Phys. Org. Chem.*, 2:63 (1964), and references cited therein). The process is acid-catalyzed and, overall, entails a dehydration preceded by a multistep equilibrium. While ketimines are formed at slower rates than aldimines due to allylic 1,3-strain, for simple alkyloxyamines the ketone-ketimine equilibrium is largely shifted towards dehydration (FIG. 1).

Example 1

Figure 2:
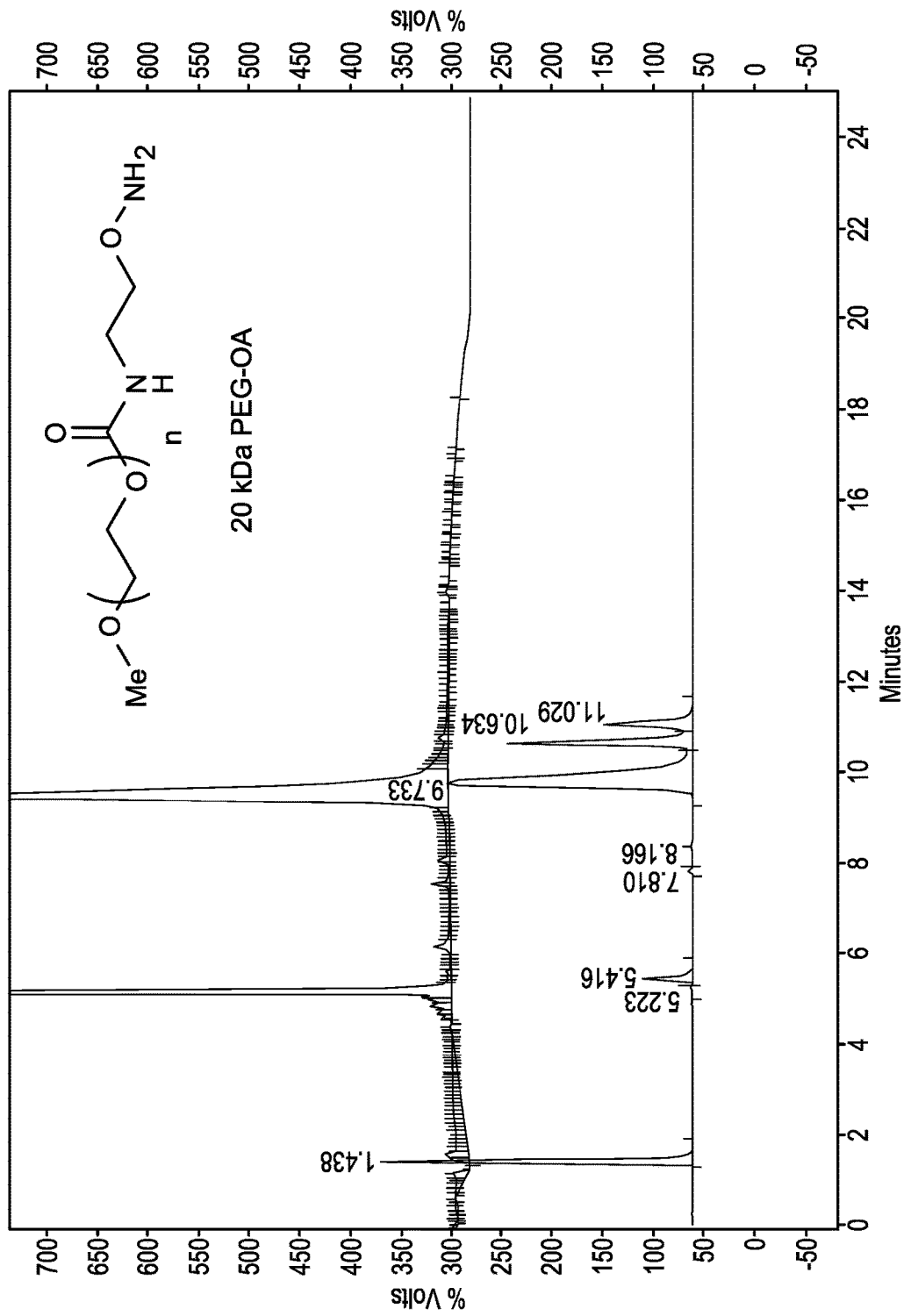
FIG. 2: Chromatogram for the PEGylation of Relaxin (4 mg/mL in water) with 20 kDa PEG-OA reagent.

Study to Investigate the Decomposition of the PEGylating Reagent as a Potential Cause for Reaction Stalling One possible cause for stalling of the PEGylation could result from decomposition of the PEGylating reagent. As the PEG reagent is not UV active it requires a different detection method to monitor its fate during the reaction. Evaporative light scattering detection involves passing the HPLC mobile phase through a nebulizer to remove the solvent. Any solid particles that form diffract light from a laser beam in the detector, resulting in a signal. This method allows detection of any compound that forms a solid that can diffract light. As the PEGylating reagents are high molecular weight solids, they are excellent candidates for HPLC analysis using ELS detection. This is evident in FIG. 2. The UV trace is shown in green, the ELS trace is shown in black. The top chromatogram (green) is the UV trace at 210 nm, the black chromatogram is the ELS trace of the same mixture obtained in series with the UV detector. Clearly the bottom black trace provides more information, particularly with the later eluting PEG-based compounds.

Figure 3:
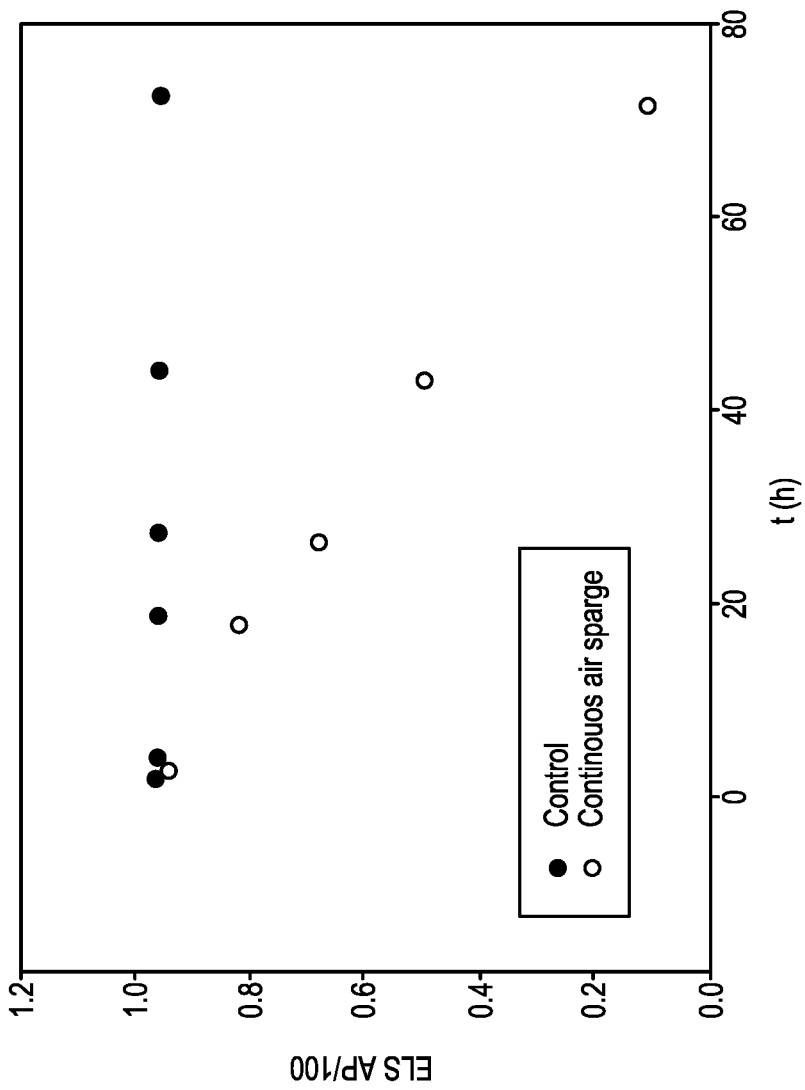
FIG. 3: Time course for the decomposition of 20 kDa PEG-OA in water when exposed to a continuous stream of air.

The latest eluting peak is not UV active and was not present at the start of the reaction. This suggested competitive decomposition of the PEGylating reagent. Indeed, this compound formed when the solution of PEGylating reagent was exposed to air (FIG. 3). The conversion of the 20 kDa PEG-OA reagent was >97% at concentrations ≈4 mg/mL and resulted in byproducts that were not reactive in the PEGylation.

As this decomposition is the result of reaction of PEGylating reagent with dissolved gas in the solvent, there should be an inverse correlation between decomposition rates and concentrations. This hypothesis matches the observation that samples of 20 kDa PEG-OA at more reaction relevant concentrations of 30-40 mg/mL were quite stable (<5% decomposition). While there may be some impact to analytical work for this project to ensure sample stability during analysis, the minimal decomposition under more reaction relevant conditions lead to the conclusion that PEG decomposition by air is not a strong cause for observed reaction stalling. The stability of the PEGylating reagent was also studied in the presence of additives employed to accelerate the PEGylation. These experiments were conducted at the expected reaction concentrations, assuming the target PEG loading of 1.2 equiv relative to Relaxin. In all cases, the decomposition of the PEGylating reagent was minimal.

Figure 4:
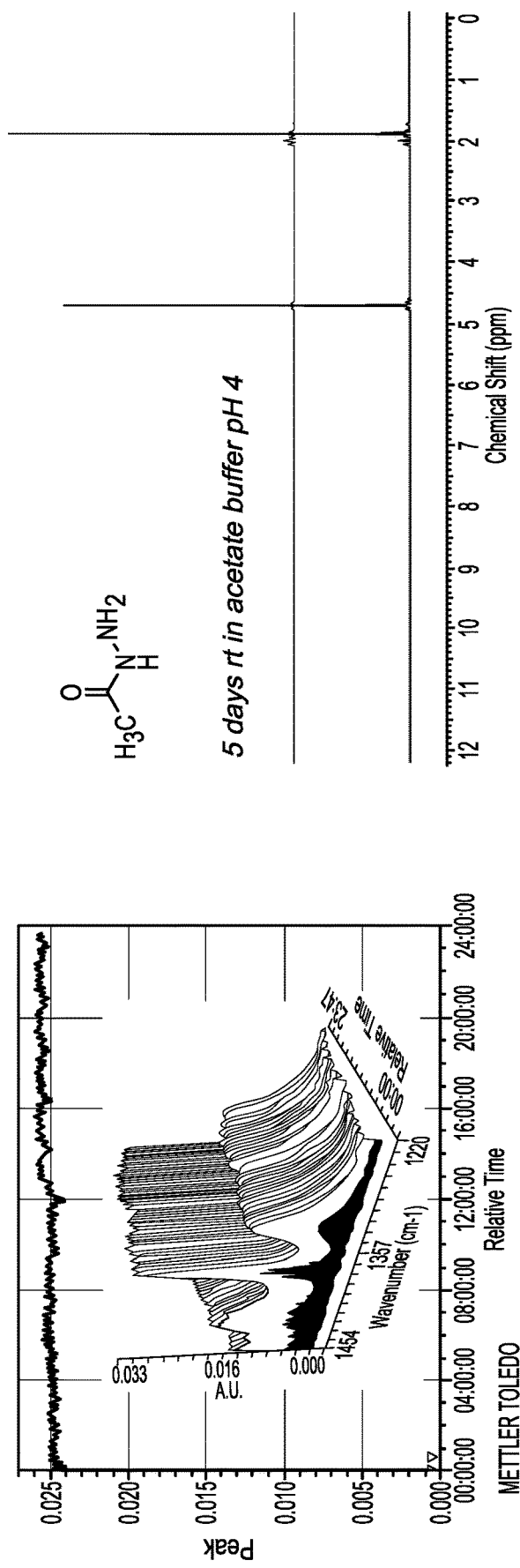
FIG. 4: Study of the stability of acetyl hydrazide using in situ IR and $^1$H NMR spectra.

Since PEGylation stalling occurs in the presence of a large excess of acetyl hydrazide as an accelerating additive, the stability of this hydrazide under the reaction conditions was tested by in situ IR and $^1$H NMR spectroscopies. The studies showed that acetyl hydrazide is stable and suggest that the excess required to promote the reaction is most likely related to the existence of equilibration and a modest acceleration relative to the uncatalyzed background process (FIG. 4).

Example 2

Studies on Screening Additives Using Dipeptide Model System (DMS)

Figure 5:
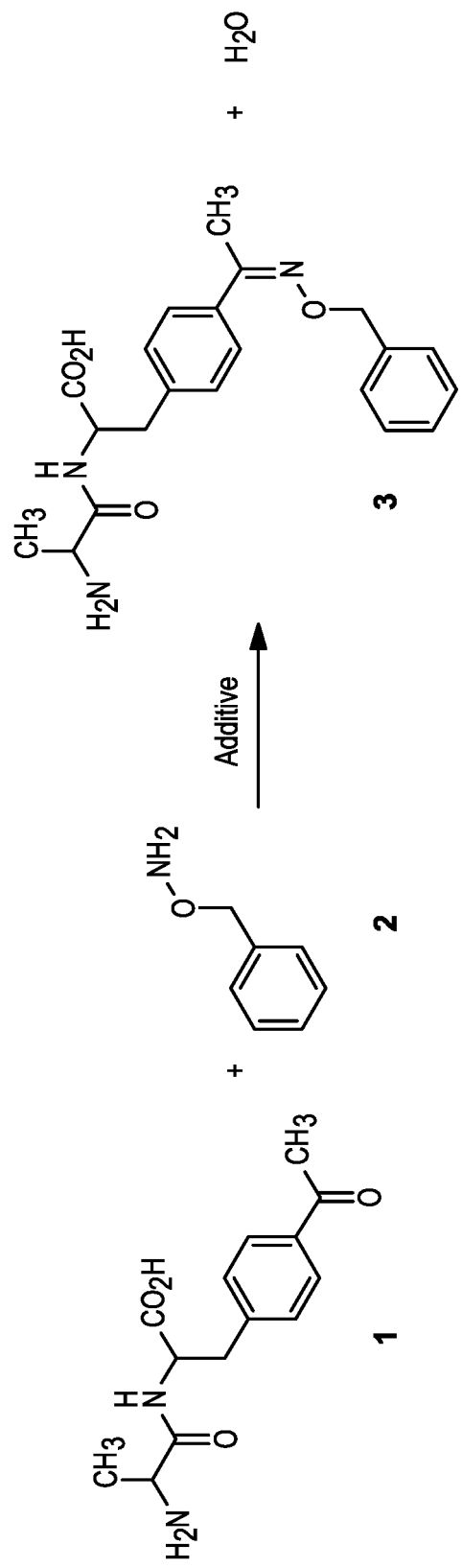
FIG. 5: Model reaction for the screening of additives. Reaction conditions: 1 (3.6 mmol) and 2 (3.6 mmol) in 1.0 mL acetate buffer (20 mM, pH 4.0) at room temperature (23° C.).

Initial efforts to find additives that accelerated the reaction between the pAcF ketone handle in Relaxin and an alkoxyamine involved the screening of commercially available compounds that contained activated X—NH$_2$ moieties capable of promoting the formation of their corresponding imino derivatives through dehydration. Minimum requirements for the selection of these additives were their sufficient stability and solubility under the temperature, buffer and pH conditions used to promote the PEGylation of the actual protein in aqueous medium. To simplify analytical procedures and facilitate reaction monitoring by HPLC-UV and NMR spectroscopy, the condensation between dipeptide Ala-pAcF (1) and O-phenylhydroxylamine (2, refer FIG. 5) was chosen as a model transformation that could guide the additive choice. In a subsequent step, additives that improved the model reaction would be tested in the PEGylation of Relaxin and FGF21. Provided in FIG. 5 is a model reaction for the screening of additives. Reaction conditions: 1 (3.6 mmol) and 2 (3.6 mmol) in 1.0 mL acetate buffer (20 mM, pH 4.0) at room temperature (23° C.).

Reaction rates and percent conversion were evaluated for fifty additives classified in four general categories, namely: anilines, hydrazines, hydrazides and hydrazinecarboxamines depending on the nature of the X substituent on the X—NH$_2$ moiety. Observed rates were normalized to the rate measured in the absence of additives ($k_{rel}$=1). Acetyl hydrazide ($k_{rel}$≈2) was a reference additive to establish a baseline acceptable performance; only those additives that afforded $k_{rel}$>2 and high conversions (>95%) would be considered for subsequent application and optimization in the PEGylation of Relaxin and FGF21. A summary of the results is shown in FIG. 6. The reactions were carried out in HPLC vials at room temperature without stirring to mimic protein PEGylation conditions, and aliquots were periodically drawn by the HPLC auto sampler to avoid further sample manipulation.

Hydrazides (colored in blue) and hydrazinecarboxamides (green) provided the best results. In general, anilines (red) afforded full dipeptide conversion but did not accelerate the reaction. Moreover, most anilines promoted high levels of undesired epimerization. Hydrazines (yellow) formed large amounts of hydrazone under the reaction conditions and were discarded for further study. Aromatic hydrazides and secondary hydrazinecarboxamines yielded up to five-fold rate accelerations as well as high conversions that stalled at approximately 95% of dipeptide consumption. In particular, the screening led to the finding of morpholine-4-carbohydrazide (MCH, 4) and p-aminobenzoic hydrazide (PABH, 7) as optimal reagents to promote the transformation. Based on their performance, solubility at pH 4, commercial availability and cost, PABH and MCH were further evaluated in the PEGylation of Relaxin and FGF21 (vide infra).

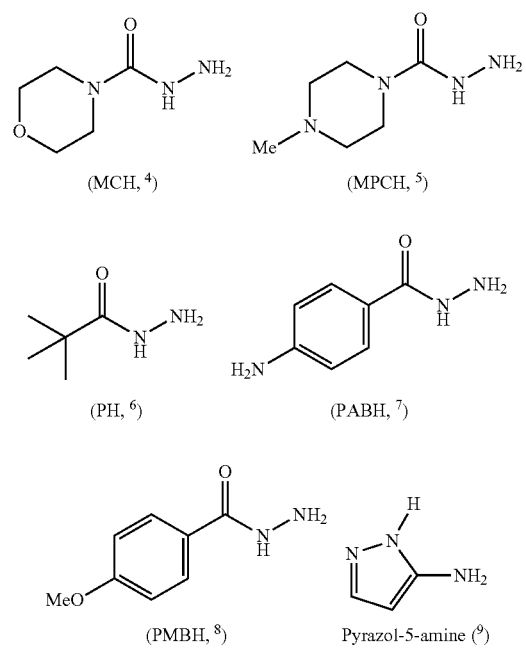

With this information in hand, attempts to circumvent reaction stalling focused on three aspects: (a) the addition of variable amounts of additive, (b) the effect of chaotropic agents, and (c) the combination of additives. Initially, studies were performed with model dipeptide and acetyl hydrazide to ascertain intrinsic trends in reactivity. Monitoring reaction rates at varying amounts of acetyl hydrazide revealed saturation kinetics in additive, indicating that the rate enhancement reaches a threshold value at high concentrations of reagent (Scheme 1).

Scheme 1
Ketone-ketoxime Equilibration Determined by NMR Spectroscopy

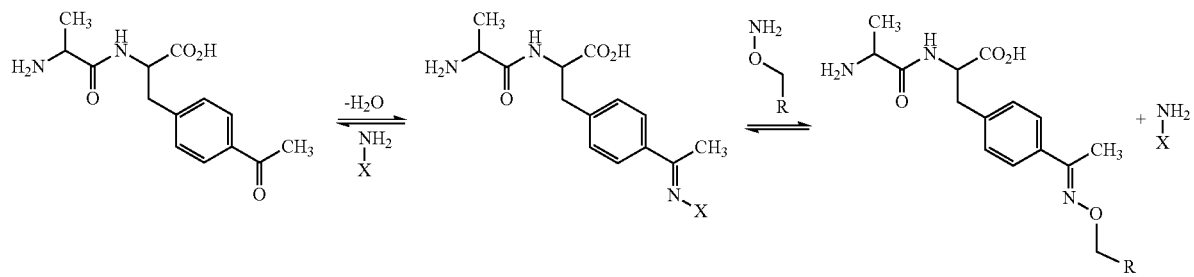

Figure 8:
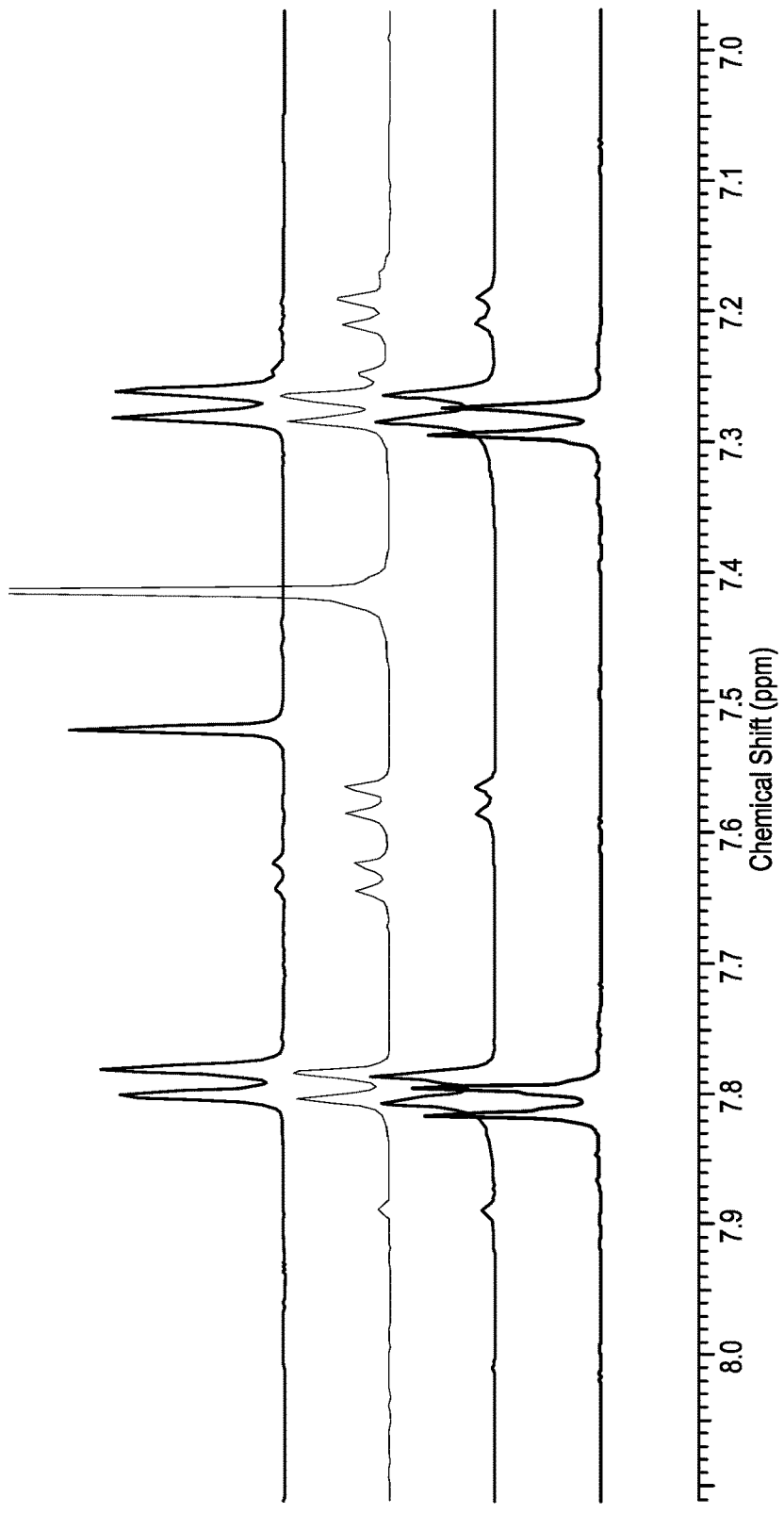
FIG. 8: Aromatic region of the $^1$H NMR spectra of samples containing dipeptide 1 (a) (blue) with (b) 1 equiv MCH (green); (c) 1 equiv MCH, and 1 equiv pyrazoleamine (grey); (d) 1 equiv pyrazoleamine (red). Synergistic effect between MCH and pyrazoleamine additives yields mixtures with higher concentration of active intermediates relative to samples containing only one additive.

Moreover, growing concentrations of acetyl hydrazide promoted higher stalling levels in agreement with a general mechanism involving a multistep sequence of reversible imine transfer reactions. In the presence of an accelerating additive, such mechanism pointed towards the possibility of achieving better conversions by shifting the apparent equilibrium towards dehydration. Empirical attempts to modify this equilibrium through changes in the reaction medium were unsuccessful. For example, the addition of 6M urea or $NH_4Cl$ did not accelerate the reaction nor affected the original conversion levels. The screening of certain anilines resulted in complete conversion without acceleration and envisioned that the combination of these anilines with an accelerating additive could help extend substrate conversion. Indeed, the use of a mixture of acetyl hydrazide and pyrazoleamine 9 led to faster reaction profiles and nearly complete conversions (FIG. 6). $^1$H NMR analysis of mixtures containing equimolar amounts of dipeptide, pyrazoleamine, MCH additive, or a mixture of MCH and pyrazoleamine revealed a synergistic growth of the imine and hydrazone intermediates for the samples containing the mixture and suggested that the positive effect of combining an accelerating additive and an aniline correlates with a shift of the equilibrium en route to the reaction intermediates (FIG. 8).

Analogous $^1$H NMR spectroscopic studies using PABH, an additive that contains both the hydrazide and aniline moieties, show the prevalent formation of a single hydrazone intermediate in agreement with DFT calculations. Under neutral conditions, computations at the B3LYP/6-31G(d) level of theory favor the formation of the hydrazone between pAcF and PABH rather than its isostructural imine by 3 kcal/mol (Scheme 2).

Scheme 2
B3LYP/6-31G(d) Geometries and Energies for the Formation of the Hydrazone and Imine Intermediate of pAcF Under Neutral Conditions

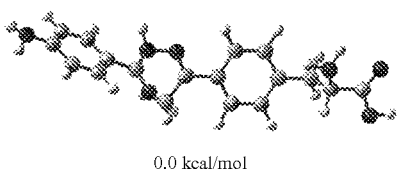

0.0 kcal/mol

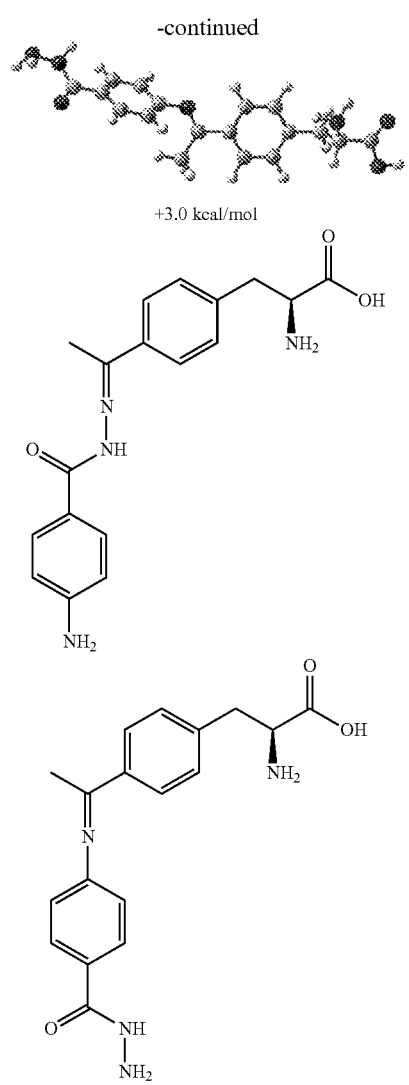

Protonation of the amino acid —$NH_2$ ($pK_a \approx 9$), supports hydrazone formation by $\approx 9$ kcal/mol. Double protonation (pKa: aniline$\approx 2.5$, hydrazide <2) favors imine formation by $\approx 1.0$ kcal/mol. Although the reaction is not run at such low pH values, DFT calculations indicate that the dehydration is highly sensitive to pH variations and H-bonding effects.

Figure 9:
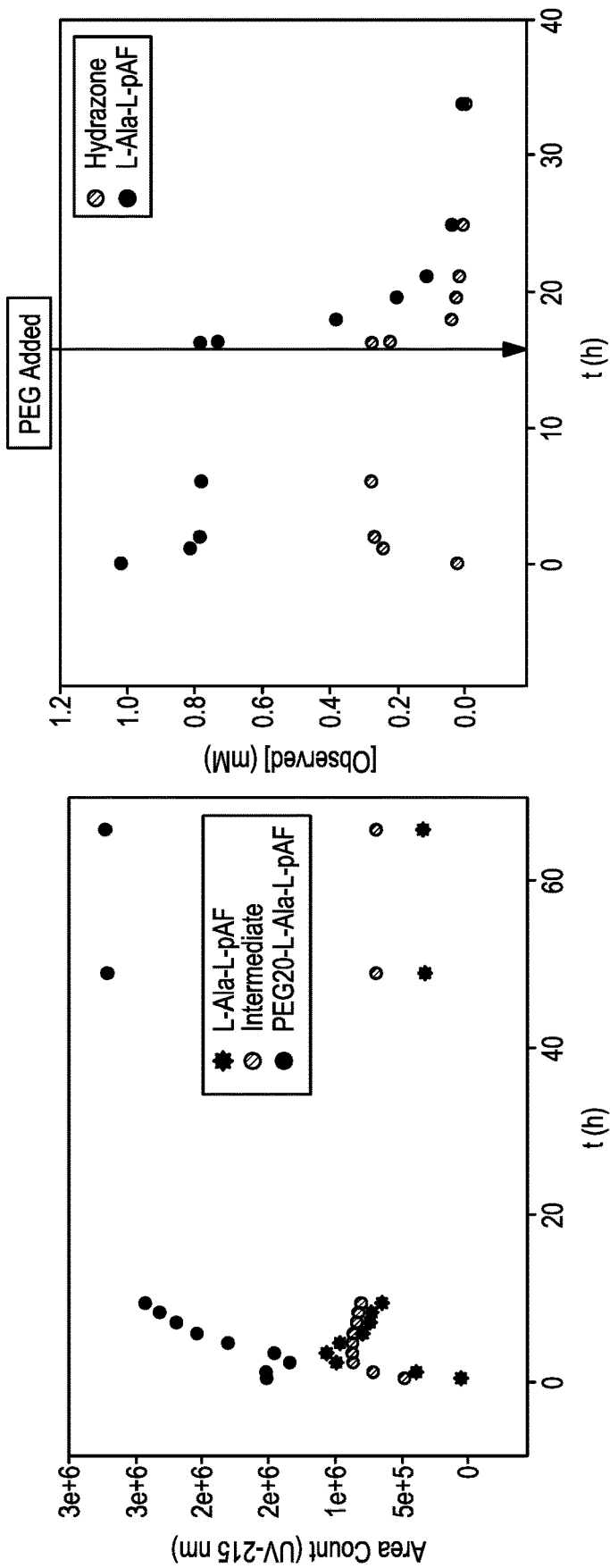
FIG. 9: Left: PEGylation of the dipeptide 1 with 30 equiv PABH and 1.2 equiv 20 kDa PEG-OA; the hydrazone intermediate is tracked as the green points. Right: PEGylation reaction in which 1.2 equiv PEGylating reagent were added after equilibrating the dipeptide with 30 equiv PABH overnight.

The hydrazone intermediate could be monitored during the PEGylation of the dipeptide 1 with PABH (FIG. 9).

Figure 11:
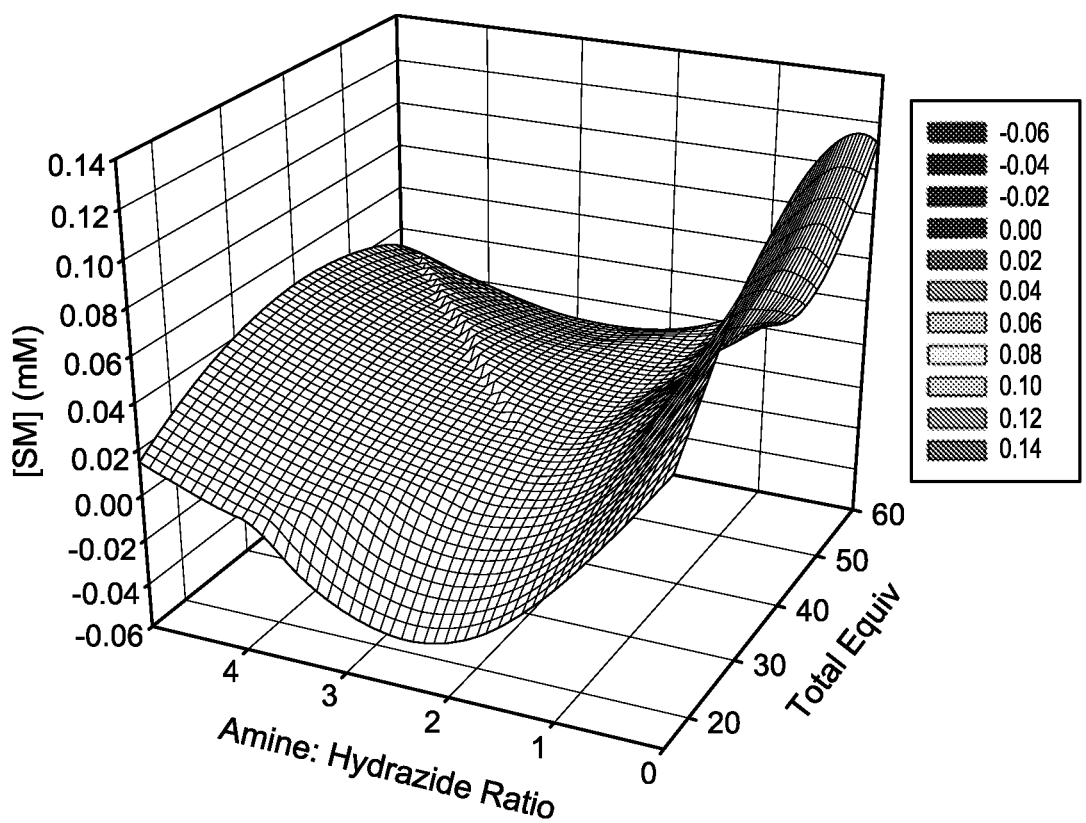
FIG. 11: Plot of remaining dipeptide 1 at the end of the reaction, versus total equivalents additive and pyrazoleamine: PABH ratio.

Control experiments that equilibrated mixtures of dipeptide 1 with PABH overnight in the absence of PEGylating reagent showed the formation of the hydrazone as well as its rapid consumption upon addition of 20 kDa PEG-OA to give the desired product. Further examination of hydrazone formation in the presence of amine additives (e.g., pyrazoleamine, FIG. 10) suggested that the extent of hydrazone formation is linked to the pyrazoleamine: PABH ratio used in the reaction. Interestingly, the extent of hydrazone formation does not correlate with reaction rates or conversions in a simple manner. In the model dipeptide system, a pyrazoleamine: PABH ratio of 1:1 was optimal for formation of the hydrazone. However, in the case of reaction rates, optimum conditions corresponded with a 1:2 ratio amine: hydrazide. The need for higher amounts of hydrazide relative to amine is supported by the preliminary screening in which hydrazides were observed to provide much higher reaction rates than the amine additives. On the other hand, a 3:1 ratio of amine:hydrazide was optimal for dipeptide conversion consistent with (a) the observation of significant amounts of hydrazone intermediate remaining at the end of the reaction at low amine:hydrazide ratio and (b) the reversal of the reaction detected upon addition of "kicker charges" of the hydrazide additive. In the experiments presented above, the total equivalents are the sum of the PBAH and pyrazoleamine. The effect of changes in the total equivalents of additive was addressed via a series of experiments run varying both the amine:hydrazide ratio as well as the total equivalents of combined additives. The results are summarized in FIG. 11. The curvature in the figure suggests that the cooperative effect between the amine and hydrazide is complex and optimization of the reaction conditions may require consideration of not only the total equivalents of the additives, but the ratio between the two.

Example 3

Additive Accelerated PEGylations of Proteins—Relaxin and FGF21

Application of the lessons learned in the model system to the PEGylation of Relaxin and FGF21 aimed to decrease the number of equivalents of 20 kDa PEG-OA to a maximum of 1.2 equiv as well as shortening reaction times at room temperature without compromising reaction yields or quality of the product. Towards this end, tested the additives identified in the model reaction with Relaxin under reaction conditions initially developed from cursory investigations. PEGylation of Relaxin (21 mg/mL in 20 mM AcONa at pH 4.0) with 1.5 equiv PEG-OA afforded good conversions ($\approx$90%) after 24 h at room temperature in the presence of 30 equiv acetyl hydrazide or MCH. In the absence of catalyst, under identical conditions, the reaction gave significantly lower conversions ($\approx$75%). Consistent with the model system studies, the PEGylation was accelerated by the additives, and the reaction with MCH was two-fold faster than the reaction with acetyl hydrazide. Moreover, the equilibration proposed in FIG. 6 found support in the following observations: (a) catalyzed reactions stalled at comparable conversions, (b) once stalled, addition of 30 equiv extra additive decreased conversion levels, and (c) once stalled, addition of 0.5 equiv PEG-OA took the reaction to higher conversion ($\approx$95%). Trends noticed for anilines in the model reaction translated to the PEGylation of Relaxin: the addition of 30 equiv pyrazoleamine transformed most of the Relaxin starting material without acceleration and, combining MCH with pyrazoleamine yielded 95% conversion in only 8 h. Efforts to optimize the reaction conditions exposed a complex interplay between the variables and encouraged the application of DoE studies to gain deeper insight (Example 4). For example, higher or lower amounts of MCH mixed with 30 equiv pyrazoleamine did not improve conversion, and the use of higher temperatures did not promote faster reactions (FIG. 12). Decreasing the charge of PEG-OA to 1.2 equiv caused stalling at $\approx$85-90% conversion under the conditions optimized for 1.5 equiv in the presence of the additives MCH, MPCH (5) or PH (6). However, in contrast with its negligible effect in the model system, the use of MCH in urea 6M advanced reaction completion up to $\approx$95% (FIG. 12).

Figure 14:
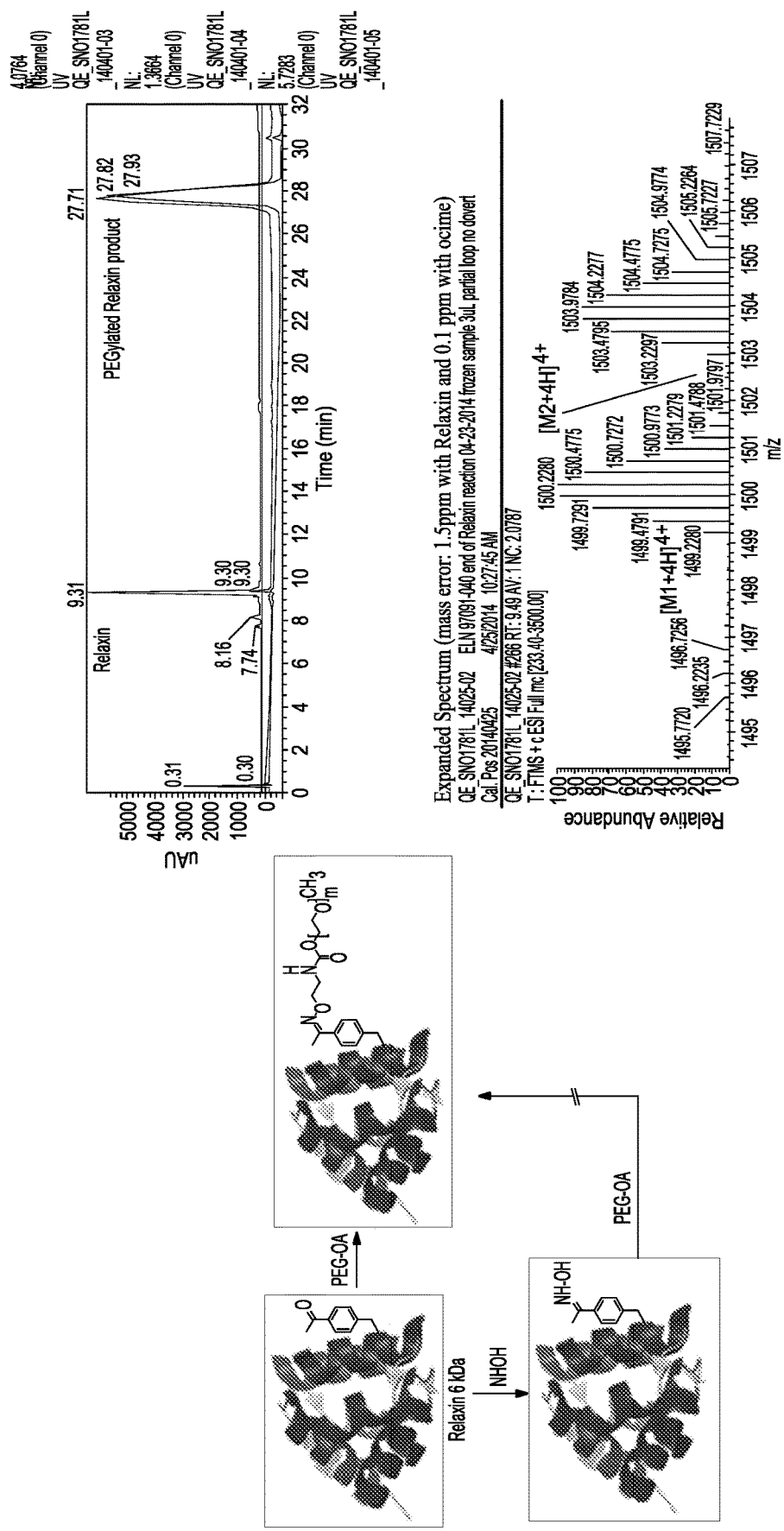
FIG. 14: HRMS analysis of a PEGylation of Relaxin accelerated by MCH at its endpoint. The oxime peak overlaps with the residual Relaxin. The 0.04 min delay for the Relaxin peak is due to the reaction matrix effect on chromatographic behavior rather than a late-eluting impurity.

Advancement of the PEGylation to completion, however, uncovered the formation of an impurity with the same retention time as the Relaxin starting material but unreactive in the presence of PEGylating reagent. HRMS studies indicated that the impurity corresponded to the oxime at the pAcF N-terminal residue and spiking $NH_2OH$ confirmed that the impurity was unproductive towards PEGylation (FIG. 13). Two hypotheses were postulated to explain the source of $NH_2OH$, namely: (a) its presence as an input impurity in the PEGylating reagent, and (b) its formation during the course of the PEGylation reaction. Careful analysis of the PEG-OA demonstrated that $NH_2OH$ levels in the starting materials were <0.05 ppm and disproved the first hypothesis. In agreement with degradation of the PEGylating reagent during the reaction, monitoring the formation of the oxime impurity showed its unambiguous growth throughout the PEGylation (FIG. 14). A systematic HRMS study of additives 4-9 indicated that MCH and MPCH promoted decomposition of the PEG-OA, whereas acetyl hydrazide, PH, PABH, PMBH, and pyrazoleamine did not. Consequently, in the optimization of PEGylations mediated by PABH since PABH affords conversions comparable to those of MCH (FIG. 6) and its cost is much lower than the latter (1 U$/g vs 60 U$/g). Optimized conditions involved the use of 30 equiv PABH and 60 equiv pyrazoleamine. These results would be subsequently confirmed by DoE studies.

Figure 19:
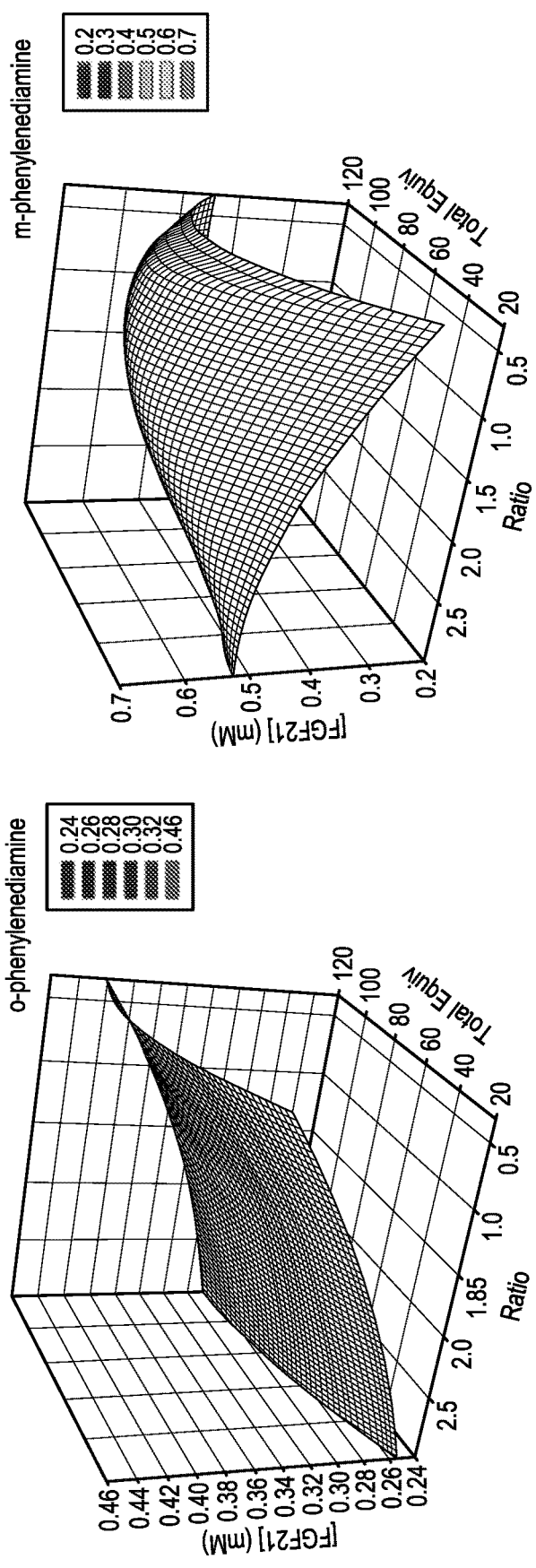
FIG. 19: PEGylation results for o- and m-phenylenediamine illustrating the curvature of the plot of total equiv versus amine:PABH ratio versus final FGF21 concentration. Left: o-phenylenediamine. Right: m-phenylenediamine.

A revision of the effect of anilines upon reaction conversion observed during the screening in the model system showed that, in addition to pyrazoleamine, three amines were able to advance completion levels. These were m-phenylenediamine, ethylenediamine, and 3,5-diaminobenzoic acid. Using 1.2 equiv PEG-OA and 30 equiv PABH, the addition of 60 equiv amine afforded conversions 95% (FIG. 19). Lower additive stoichiometries resulted in lower conversions at short times 90%) but slowly achieved higher conversions at 24 h.

Example 4

DoE Studies to Evaluate the Interactions Between Different Additive Combinations The interplay between amine and hydrazide additives was further explored for the PEGylation of Relaxin and FGF21 using a DOE approach that took into account four variables, namely (a) the identity of the hydrazide, (b) the identity of the amine, (c) total equivalents of additives, and (d) amine: hydrazide ratio of the additives used. The studies were performed with Relaxin and FGF21 to examine the effect of the amine:hydrazide molar ratio and PEG-OA loadings on rates and conversions, and analyze a variety of amines previously identified in the model system (FIG. 6). The results of these experiments pointed to a complex interplay between the amine:hydrazide ratio and indicated that reaction optimization requires careful consideration of the type of amine as well as the substrate protein.

Figure 7:
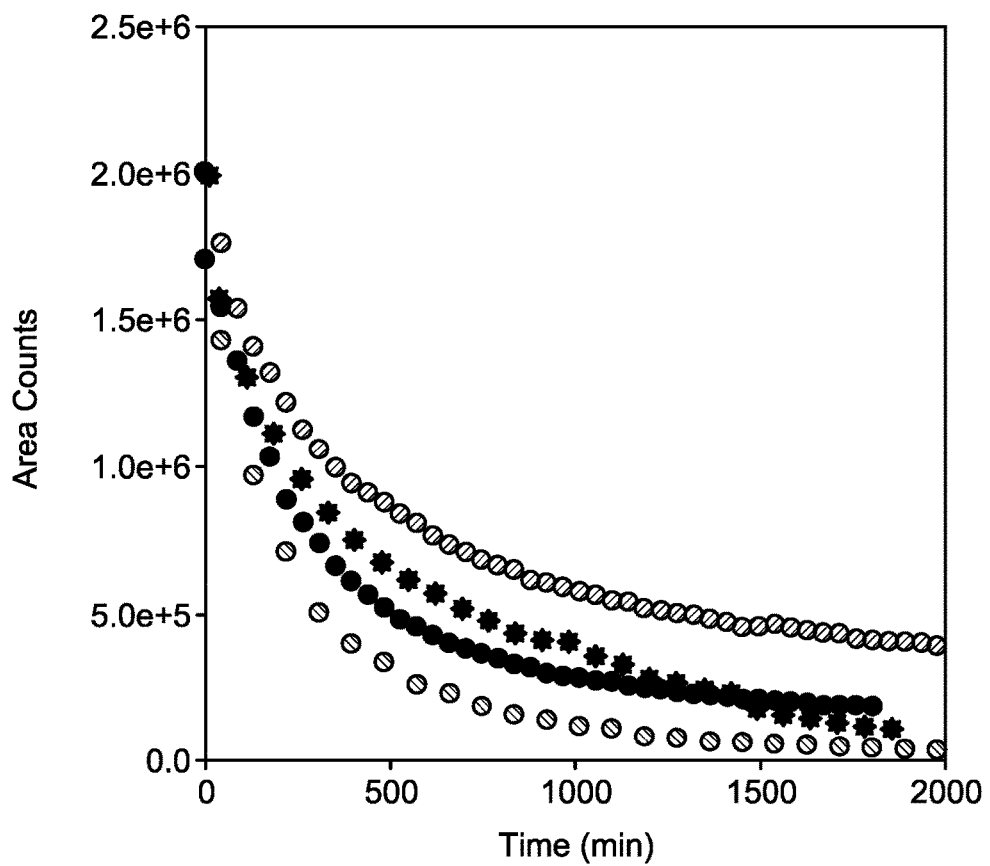
FIG. 7: Time course for the reaction of dipeptide 1 with O-benzylhydroxylamine (2) in the presence of (a) 1 equiv pyrazoleamine (red); (b) 1 equiv MCH (blue); (c) 1 equiv pyrazoleamine and 1 equiv MCH (green). The reaction profile obtained in the absence of additives is shown in grey.
Figure 17:
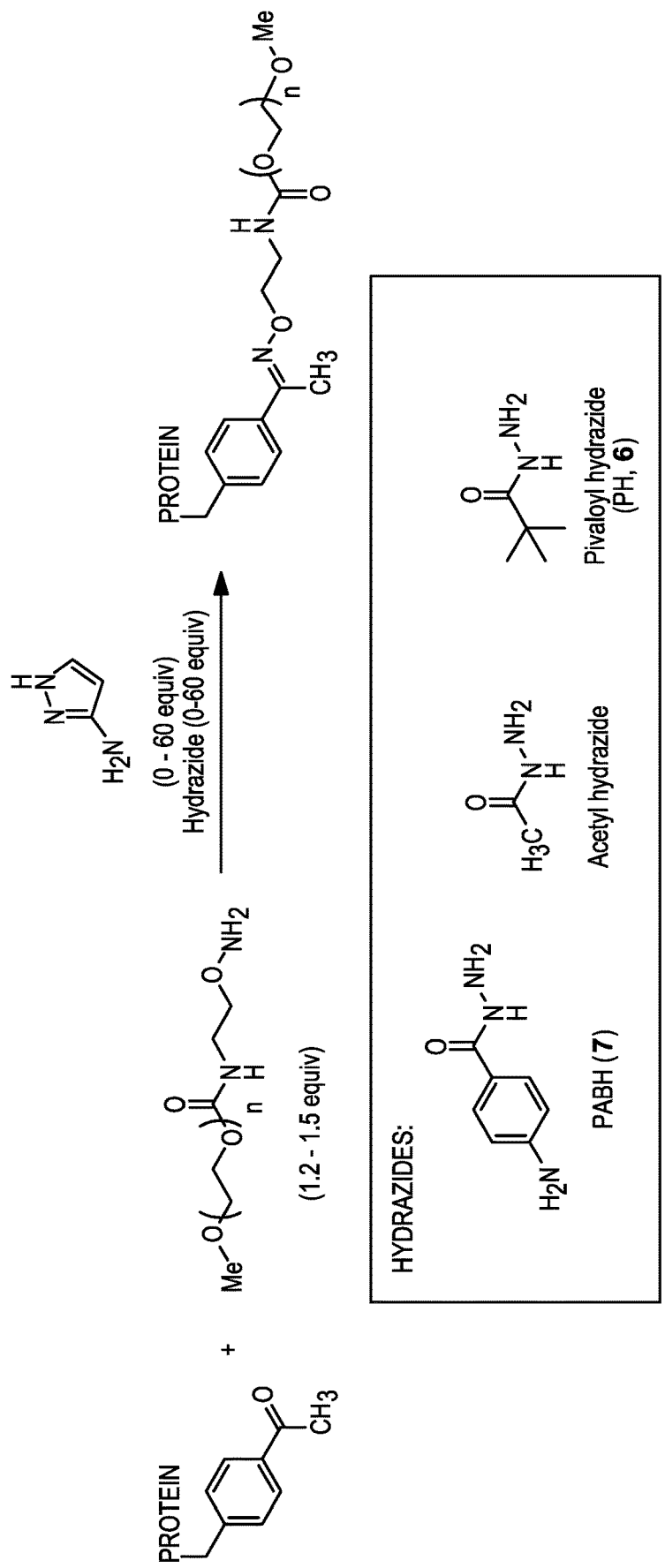
FIG. 17: Scheme for the preliminary PEGylation screening.
Figure 18:
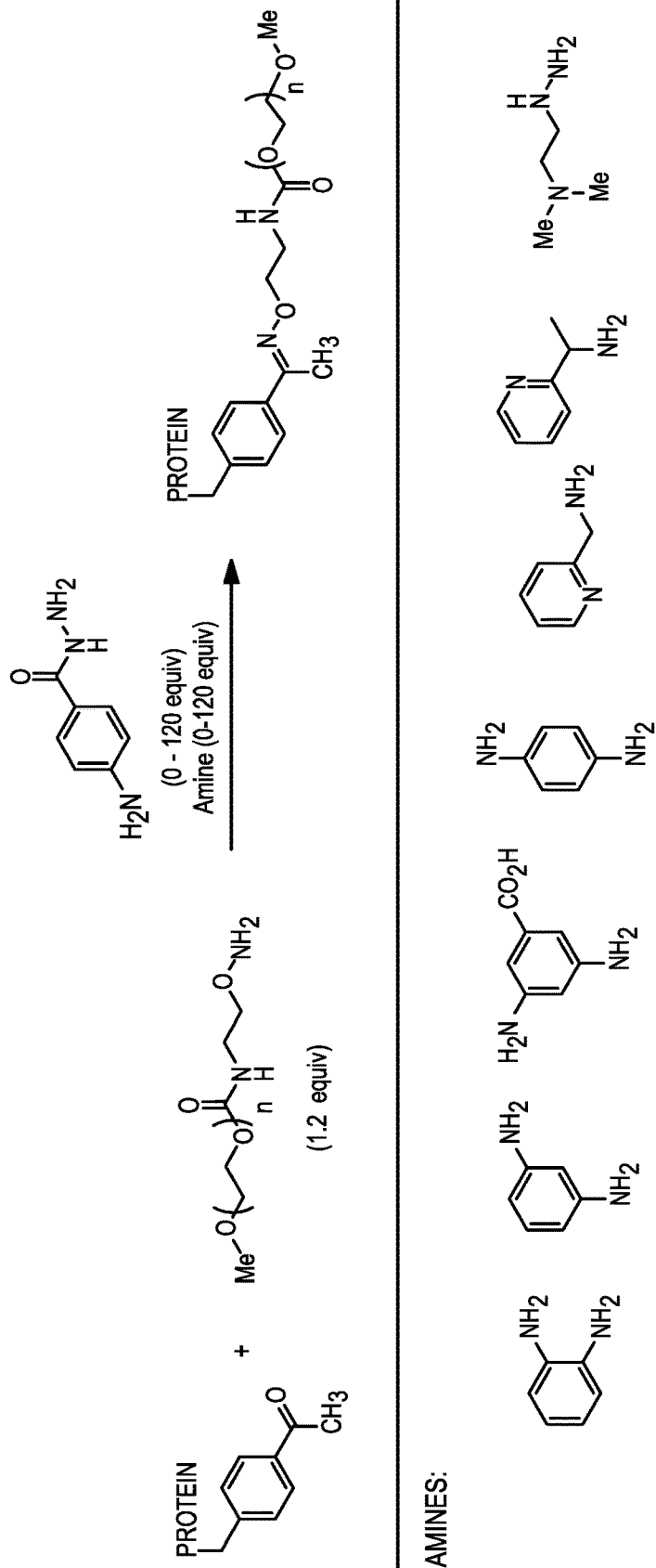
FIG. 18: Scheme for the PEGylation of Relaxin and FGF21 with different amines.

In the first round of screening (Table 1), we utilized PABH, acetyl hydrazide, and pivalic hydrazide in combination with pyrazoleamine for the PEGylation of both Relaxin and FGF21 (FIG. 17). PEG-OA equivalents and urea concentration were also considered. Most of the additive systems in this screen gave good performance. In agreement with previous studies (FIGS. 7 and 12), the 2:1 amine:hydrazide system was among the best for promoting high conversion. Although pivalic hydrazide was an excellent hydrazide additive that could promote high conversion and fast reaction rates, new impurities were observed in the reaction mixtures that were not present when PABH was used.

TABLE 1

Results from Preliminary Screening of the PEGylation of Relaxin

| Pyrazoleamine (equiv) | Hydrazide | Hydrazide (equiv) | Conversion (%) |
|---|---|---|---|
| 60 | Pivalic hydrazide | 30 | 98 |
| 60 | PABH | 30 | 96 |
| 0 | Pivalic hydrazide | 60 | 96 |
| 30 | Acetyl hydrazide | 10 | 96 |

This screen was repeated using FGF21 with similar results (Table 2). PABH proved to be the standout additive to accelerate the reaction and, as one of the goals of this initiative was to develop a general PEGylation method that can be applied to abroad range of protein systems, PABH was selected for further study. Additional support for the use of PABH as the hydrazide component was the fact that it is negative in AMES testing unlike acetyl hydrazide, which is a known potent mutagen (Bhide, S. V. et al., *Cancer Lett.*, 23:235 (1984)).

TABLE 2

Results from the Preliminary Screening of the PEGylation of FGF21

| Pyrazoleamine (equiv) | Hydrazide | Hydrazide (equiv) | Conversion (%) |
|---|---|---|---|
| 0 | PABH | 30 | 91 |
| 60 | PABH | 60 | 89 |
| 30 | PABH | 30 | 88 |
| 30 | Pivalic hydrazide | 60 | 83 |
| 10 | Acetyl hydrazide | 60 | 82 |
| 60 | Pivalic hydrazide | 10 | 80 |
| 0 | Acetyl hydrazide | 10 | 77 |
| 10 | Pivalic hydrazide | 10 | 73 |
| 0 | Acetyl hydrazide | 30 | 69 |

Having chosen PABH as the hydrazide, it was screened in combination with a broader scope of amines, using both Relaxin and FGF21 proteins (Scheme 3). For these experiments the following considerations were made: (a) amines previously tested in the model system (FIG. 5) would be screened, (b) total additive equivalents (sum of hydrazide and amine) would range from 20 to 120, and (c) reaction times would be limited to 24 h.

Scheme 3
Scheme for the PEGylation of Relaxin and FGF21 with Different Amines

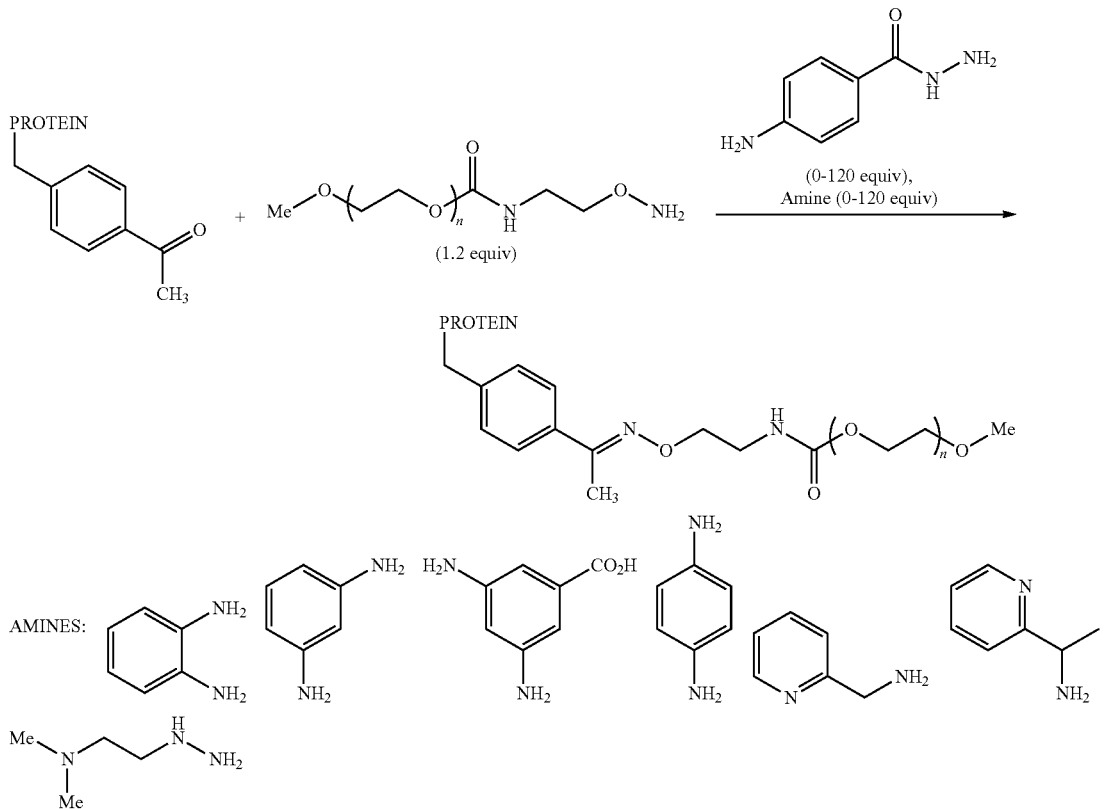

As the first DOE screening was conducted using PABH and pyrazoleamine, it was of primary interest to determine which of the amines (or class of amines) was optimum for use in additive systems with PABH. Experimental results from the screening with Relaxin and FGF21 are summarized below (Tables 3 and 4, respectively).

TABLE 3

Data from Relaxin DoE Round 2

| Amine Additive | Amine:PABH Ratio | Total Equiv | Time (h) | Conversion (%) |
|---|---|---|---|---|
| o-Phenylenediamine | 0.6 | 20 | 22.7 | 96 |
| o-Phenylenediamine | 1.7 | 50 | 21.0 | 96 |
| o-Phenylenediamine | 0.3 | 85 | 18.5 | 94 |
| o-Phenylenediamine | 0.6 | 120 | 18.4 | 94 |
| 1-Pyridin-2-yl-ethylamine | 0.3 | 20 | 22.2 | 94 |
| 1-Pyridin-2-yl-ethylamine | 3.0 | 20 | 23.7 | 93 |
| 1-Pyridin-2-yl-ethylamine | 0.3 | 120 | 22.6 | 91 |
| 1-Pyridin-2-yl-ethylamine | 3.0 | 120 | 23.5 | 88 |
| 2-(Dimethylamino)ethylhydrazine | 0.3 | 20 | 23.1 | 94 |
| 2-(Dimethylamino)ethylhydrazine | 3.0 | 20 | 23.1 | 88 |
| 2-(Dimethylamino)ethylhydrazine | 1.0 | 85 | 21.4 | 84 |
| 2-(Dimethylamino)ethylhydrazine | 3.0 | 120 | 19.7 | 55 |
| 3,5-Diaminobenzoic acid | 3.0 | 20 | 18.8 | 94 |
| 3,5-Diaminobenzoic acid | 1.0 | 50 | 20.1 | 95 |
| 3,5-Diaminobenzoic acid | 3.0 | 120 | 21.8 | 94 |
| 3,5-Diaminobenzoic acid | 0.3 | 120 | 23.5 | 94 |
| m-Phenylenediamine | 3.0 | 20 | 19.3 | 94 |
| m-Phenylenediamine | 0.6 | 85 | 18.9 | 94 |
| m-Phenylenediamine | 3.0 | 120 | 23.1 | 96 |
| m-Phenylenediamine | 0.3 | 120 | 19.7 | 93 |
| p-Phenylenediamine | 1.0 | 20 | 19.3 | 96 |
| p-Phenylenediamine | 3.0 | 50 | 18.9 | 96 |
| p-Phenylenediamine | 1.6 | 120 | 20.6 | 94 |

TABLE 4

Data from FGF21 Round 2

| Amine Additive | Amine:PABH Ratio | Total Equiv | Time (h) | Conversion (%) |
|---|---|---|---|---|
| o-Phenylenediamine | 0.64 | 120 | 23.5 | 60 |
| o-Phenylenediamine | 3.00 | 85 | 23.7 | 70 |
| o-Phenylenediamine | 0.33 | 85 | 24.3 | 57 |
| o-Phenylenediamine | 1.74 | 50 | 20.9 | 67 |
| o-Phenylenediamine | 0.64 | 20 | 20.5 | 64 |
| m-Phenylenediamine | 3.00 | 20 | 24.4 | 48 |
| m-Phenylenediamine | 0.33 | 120 | 24.9 | 55 |
| m-Phenylenediamine | 0.33 | 20 | 24.1 | 70 |
| m-Phenylenediamine | 0.64 | 85 | 24.7 | 37 |
| m-Phenylenediamine | 3.00 | 120 | 20.9 | 75 |
| 3,5-Diaminobenzoic acid | 3.00 | 20 | 23.9 | 55 |
| 3,5-Diaminobenzoic acid | 0.33 | 120 | 23.2 | 58 |
| 3,5-Diaminobenzoic acid | 0.33 | 20 | 22.3 | 70 |
| 3,5-Diaminobenzoic acid | 1.00 | 50 | 20.1 | 76 |
| 3,5-Diaminobenzoic acid | 3.00 | 120 | 19.7 | 77 |
| Ethylenediamine | 1.00 | 20 | 24.3 | 59 |
| Ethylenediamine | 3.00 | 50 | 24.0 | 55 |
| Ethylenediamine | 0.33 | 50 | 22.7 | 73 |
| Ethylenediamine | 0.33 | 120 | 21.4 | 77 |
| Ethylenediamine | 1.57 | 120 | 20.5 | 52 |
| 2-Picolylamine | 0.33 | 85 | 23.6 | 65 |
| 2-Picolylamine | 3.00 | 85 | 23.1 | 74 |
| 2-Picolylamine | 1.00 | 120 | 22.4 | 68 |
| 2-Picolylamine | 1.57 | 20 | 24.5 | 58 |
| 2-Picolylamine | 0.33 | 20 | 19.2 | 54 |
| 1-Pyridin-2-yl-ethylamine | 0.33 | 120 | 22.2 | 58 |
| 1-Pyridin-2-yl-ethylamine | 3.00 | 120 | 23.1 | 42 |
| 1-Pyridin-2-yl-ethylamine | 3.00 | 20 | 24.0 | 24 |
| 1-Pyridin-2-yl-ethylamine | 1.57 | 85 | 21.8 | 70 |
| 1-Pyridin-2-yl-ethylamine | 0.64 | 50 | 23.2 | 68 |
| 1-Pyridin-2-yl-ethylamine | 0.33 | 20 | 20.1 | 53 |
| 2-(Dimethylamino)ethylhydrazide | 3.00 | 20 | 22.7 | 52 |
| 2-(Dimethylamino)ethylhydrazide | 0.33 | 20 | 22.8 | 48 |
| 2-(Dimethylamino)ethylhydrazide | 0.33 | 120 | 22.8 | 70 |
| 2-(Dimethylamino)ethylhydrazide | 3.00 | 120 | 19.7 | 20 |
| 2-(Dimethylamino)ethylhydrazide | 1.00 | 85 | 19.3 | 49 |

The results for the PEGylation of Relaxin are consistent between the various amines, and conversions in general are reasonably high. On the other hand, for FGF21 3,5-diaminobenozic acid appears to be a good promoter of the PEGylation at both 1.0 and 3.0 amine:PABH ratios. Holding the total equivalents and ratio constant we get a better picture of the impact the amine has on conversions. For Relaxin this data is presented in Table 5.

TABLE 5

Effect of the Choice of Amine on Conversion for the PEGylation of Relaxin

| Amine Additive | Amine:PABH Ratio | Total Equiv | Time (h) | Conversion (%) |
|---|---|---|---|---|
| 1-Pyridin-2-yl-ethylamine | 0.33 | 120 | 28.1 | 91 |
| m-Phenylenediamine | 0.33 | 120 | 25.2 | 94 |
| 1-Pyridin-2-yl-ethylamine | 0.33 | 120 | 22.6 | 91 |
| p-Phenylenediamine | 0.33 | 120 | 25.0 | 94 |
| 3,5-Diaminobenzoic acid | 0.33 | 120 | 23.5 | 93 |
| 2-(Dimethylamino)ethylhydrazine | 0.33 | 120 | 32.1 | 88 |

For Relaxin, the impact of the amine additive is apparent, but given the high overall conversions observed, this impact is again low. For FGF21, the impact is higher (Table 6).

TABLE 6

Effect of the Choice of Amine on Conversion for the PEGylation of FGF21

| Amine Additive | Amine:PABH Ratio | Total Equiv | Time (h) | Conversion (%) |
|---|---|---|---|---|
| m-Phenylenediamine | 0.33 | 120 | 24.9 | 55 |
| 3,5-Diaminobenzoic acid | 0.33 | 120 | 23.2 | 58 |
| Ethylenediamine | 0.33 | 120 | 21.4 | 77 |
| 1-Pyridin-2-yl-ethylamine | 0.33 | 120 | 22.2 | 58 |
| 2-(Dimethylamino)ethylhydrazide | 0.33 | 120 | 22.8 | 70 |

From these data it is clear that conversion is highly dependent on the identity of the amine used in combination with PABH. Realizing these conditions do not necessarily reflect the optimum conditions for the PEGylation reaction, we sorted by conversion to arrive at the list of the top five performing additive combinations for FGF21 (Table 7).

TABLE 7

Top 5 Performing Additive Systems for the PEGylation of FGF21

| Amine Additive | Total Equiv | Amine:PABH Ratio | Time (h) | Conversion (%) |
|---|---|---|---|---|
| m-Phenylenediamine | 120 | 3.00 | 20.9 | 75 |
| 3,5-Diaminobenzoic acid | 50 | 1.00 | 20.1 | 76 |
| 3,5-Diaminobenzoic acid | 120 | 3.00 | 19.7 | 77 |
| Ethylenediamine | 120 | 0.33 | 21.4 | 77 |
| 2-Picolylamine | 85 | 3.00 | 23.1 | 74 |

Ethylenediamine and 3,5-diaminobenzoic acid were the two top performers for the PEGylation of FGF21 under the conditions screened. As 3,5-diaminobenzoic acid is a relatively inexpensive and readily available crystalline solid, it was deemed a favorite additive for the amine:PABH combination. Further support will come from the detailed analysis of total equivalents versus amine:PABH ratios. As observed in the model system, the cooperative effect of the two additives is quite complex. In fact, the curvature observed in the model system was more pronounced for the PEGylation of Relaxin and FGF21. The data and trends for FGF21 are shown in FIG. 19. Anilines o- and m-phenylenediamine were good additives when used in the PEGylation of FGF21. Interestingly, a plot of the final concentration of remaining protein versus the total equivalents and amine:PABH ratio afforded completely different results. The only structural difference between these two additives is the orientation of the amino groups.

Figure 20:
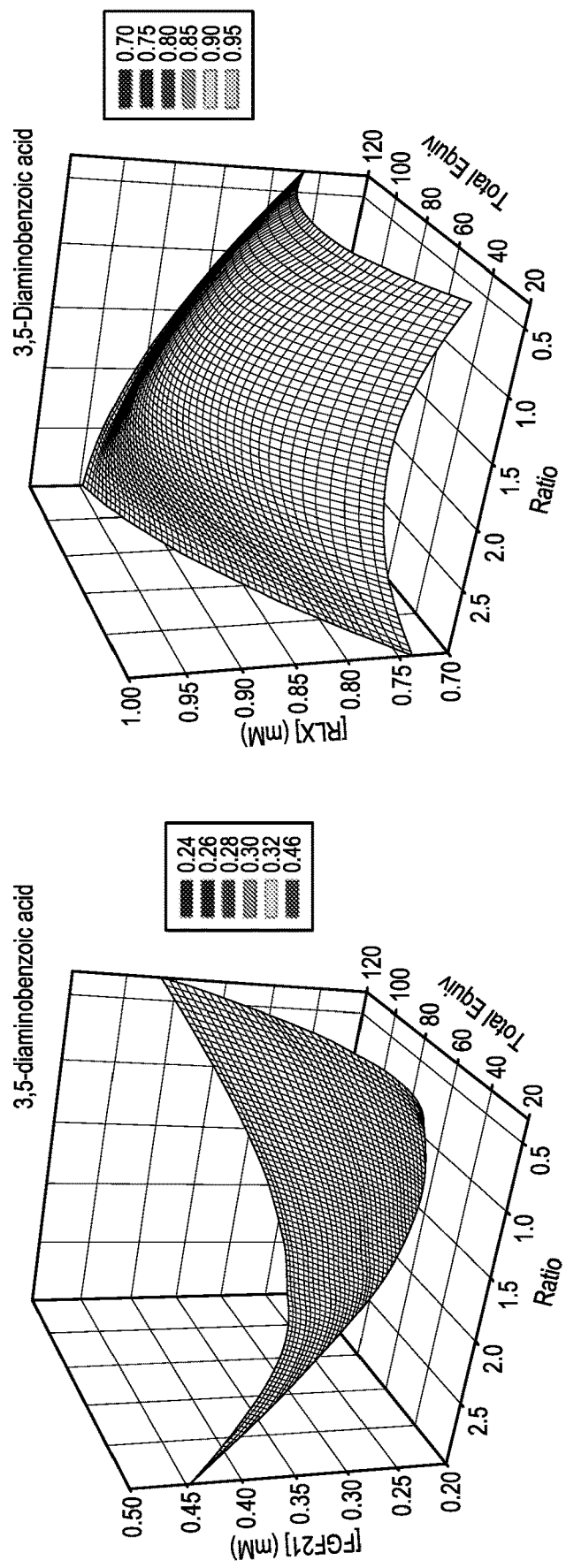
FIG. 20: Plots of total additive equivalents versus amine:PABH ratio and conversion for PEGylations using PABH and 3,5-diaminobenzoic acid. Left: FGF21 with 30 kDa PEG-OA. Right: Relaxin with 20 kDa PEG-OA.

As the z-axis is the final concentration of FGF21 in the reaction mixture, the ideal conditions will have the lowest z-axis value in the plot. For a robust process that can allow for minor differences in the reagent charges, a flat plot or a plot with a valley or well is ideal. One additive that met this premise is 3,5-diaminobenzoic acid (FIG. 20).

When used in PEGylation of Relaxin, 3,5-diaminobenzoic acid also produced high conversions in reasonable reaction times. The comparison of FIG. 20 (left and right) demonstrates that increased conversions are linked to the identity of the protein as well.

Example 5

Use of Simple Ammonium Salts

Figure 21:
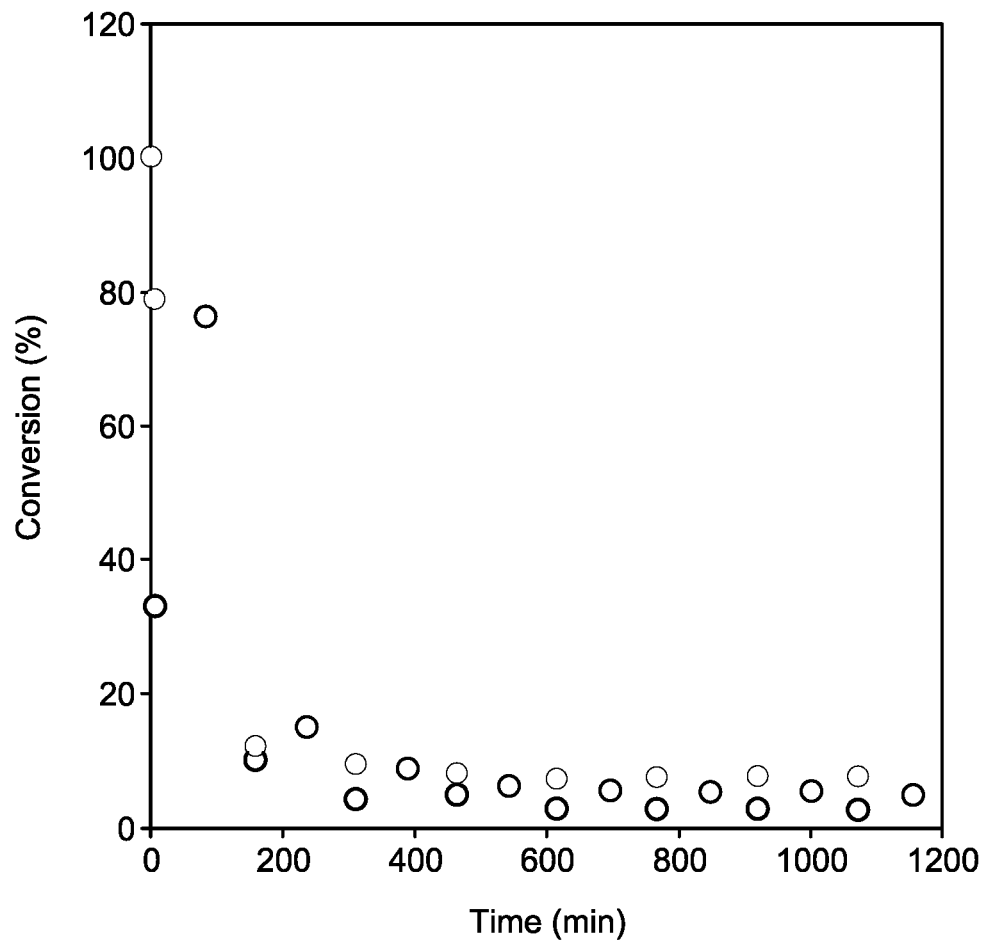
FIG. 21: Left: Time course for the reaction of Relaxin with 20 kDa PEG-OA (1.2 equiv) in the presence of 120 equiv salt and 60 equiv PABH catalyst using (a) urea 6 M (green); (b) $NH_4Cl$ (grey); and (c) $(NH_4)_2SO_4$.
Figure 22:
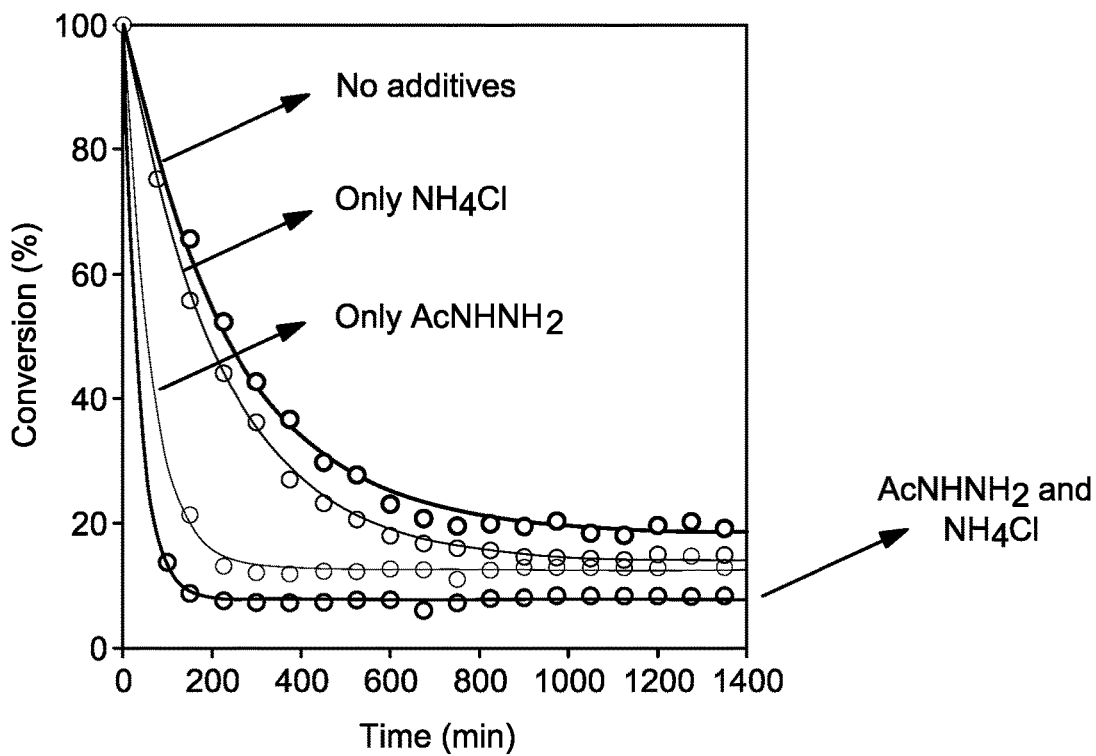
FIG. 22: Time course for the reaction of Relaxin with 20 kDa PEG-OA (1.2 equiv) in the absence of additives (blue) and the presence of: (a) 120 equiv $NH_4Cl$ (red), (b) 60 equiv acetyl hydrazide (grey), and (c) 60 equiv acetyl hydrazide and 120 equiv $NH_4Cl$ (green).

In view of the beneficial effect of amine additives at pH 4, we reckoned that simple ammonium salts could also improve the PEGylation of Relaxin. Towards this end, a series of experiments with varying amounts of PABH and $NH_4OAc$ or $NH_4Cl$ were carried out that revealed the superiority of the combination of 60 equiv PABH and 120 equiv $NH_4Cl$ to afford the best conversion yet observed at 10 h (97%, Table 8). Interestingly, re-examination of the reaction of the model dipeptide in the presence of $NH_4Cl$ provided a profile that was identical to the profile observed without $NH_4Cl$, suggesting that the effect of $NH_4Cl$ can be associated to changes in the structure of Relaxin. Indeed, the addition of known chaotropic reagents such as urea or $(NH_4)_2SO_4$ afforded comparable results (FIG. 21). The positive effect of $NH_4Cl$ seems general and reappears in the PEGylation of Relaxin without hydrazide additive or in the presence of acetyl hydrazide (FIG. 22).

TABLE 8

Conversions for the Screening of Additive Amounts and Simple Ammonium Salts

| Reaction | Additive | Salt | Conversion (10 h) |
|---|---|---|---|
| 1 | 30 equiv pNHPhHydrazide | 60 equiv NH$_4$OAc | 90% |
| 2 | 30 equiv pNHPhHydrazide | 120 equiv NH$_4$OAc | 94% (x3) |
| 3 | 60 equiv pNHPhHydrazide | 60 equiv NH$_4$OAc | 95% |
| 4 | 60 equiv pNHPhHydrazide | 120 equiv NH$_4$OAc | 92% |
| 5 | 60 equiv pNHPhHydrazide | 120 equiv NH$_4$Cl | 97% |
| 6 | 30 equiv pNHPhHydrazide | 60 equiv NH$_4$Cl | 95% |

Figure 23:
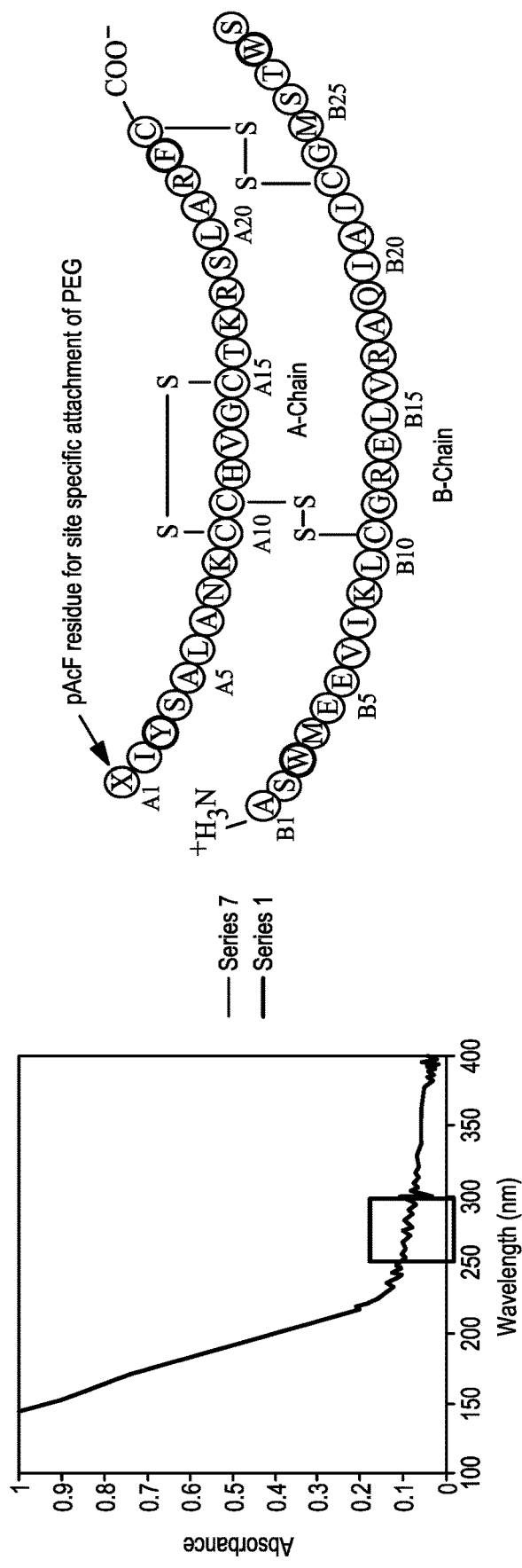
FIG. 23: Left: UV spectra of Relaxin before and after the addition of 120 equiv $NH_4Cl$ (blue and red, respectively). Right: Amino acid sequence of Relaxin highlighting the aromatic resides in red.
Figure 24:
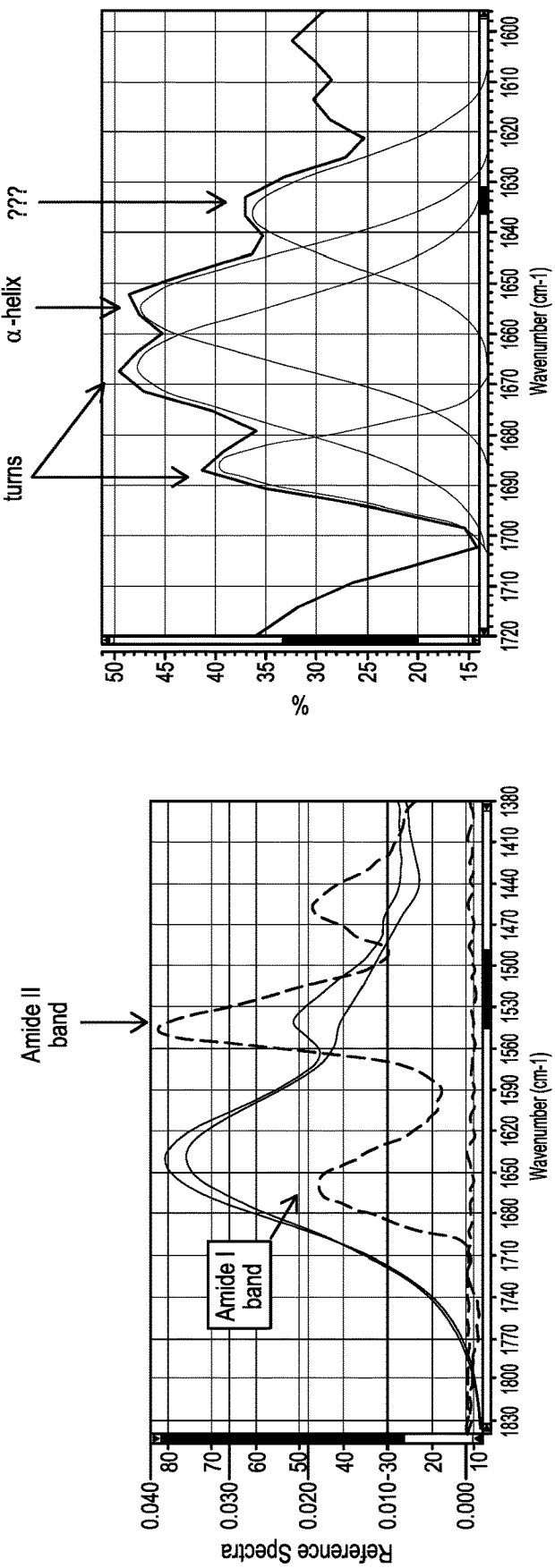
FIG. 24: Left: IR spectra of Relaxin before and after the addition of 120 equiv $NH_4Cl$ (blue and purple, respectively). Right: Inset of the IR spectrum after addition of 120 equiv $NH_4Cl$ with tentative assignments for the structural changes.

Spectroscopic studies seeking a better understanding of the origins of the NH$_4$Cl effect suggested that the salt modifies the conformation of Relaxin in solution. While UV spectroscopic analysis could not detect variations in the absorbance of the aromatic residues (260-290 nm) upon addition of 120 equiv NH$_4$Cl (FIG. 23), IR spectroscopy indicated the existence of structural modifications on the amide II band H-bonding (FIG. 24). Presumably, the failure of the UV analysis to detect changes on the aromatic residues can be traced to the distal location of amino acids Tyr(Y), Phe(F), and Trp(W) in Relaxin, which largely exposes the residues to solvent and lack any significant intramolecular interactions.

Figure 25:
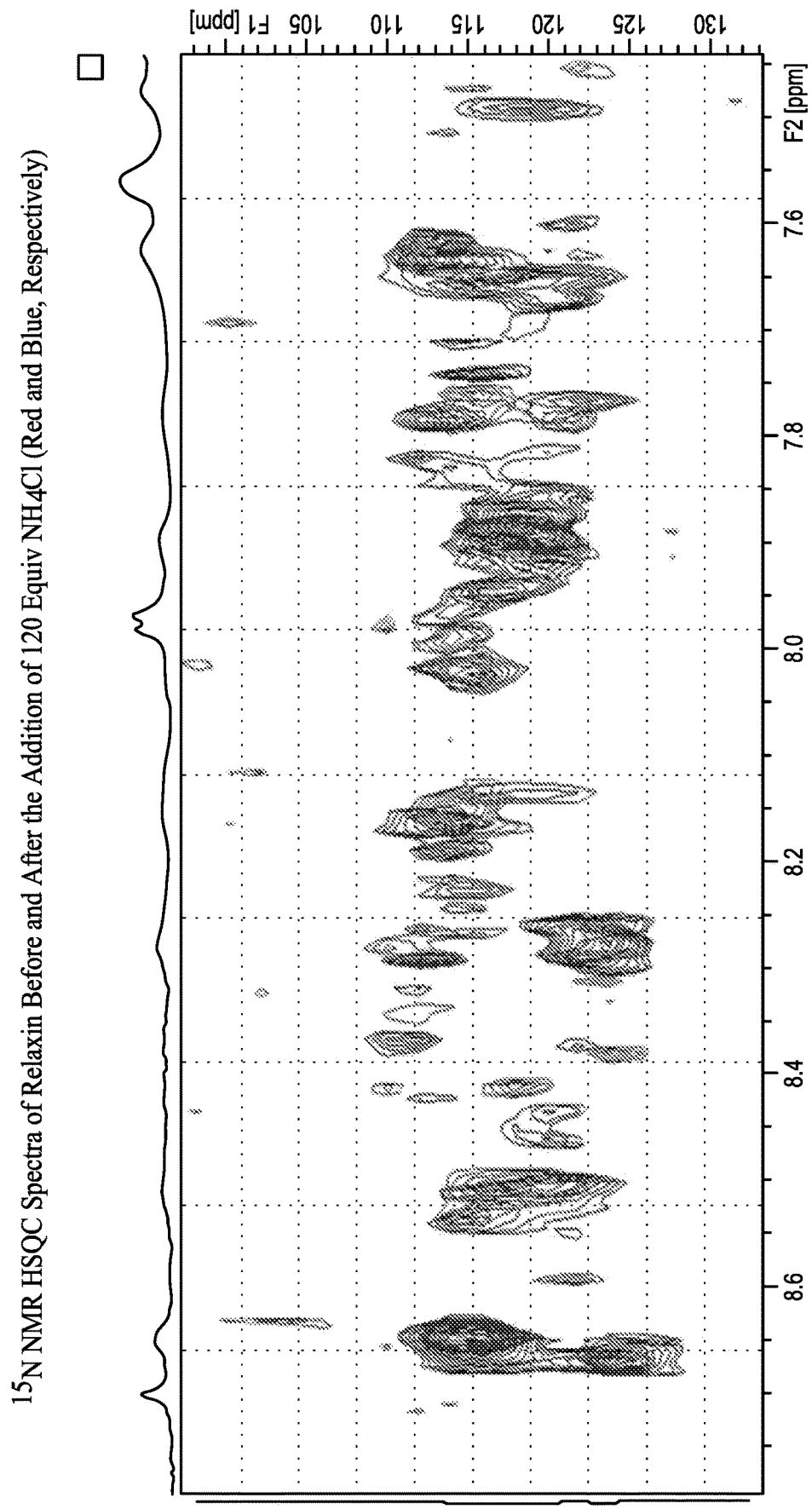
FIG. 25: $^{15}N$ NMR HSQC spectra of Relaxin before and after the addition of 120 equiv $NH_4Cl$ (red and blue, respectively).
Figure 26:
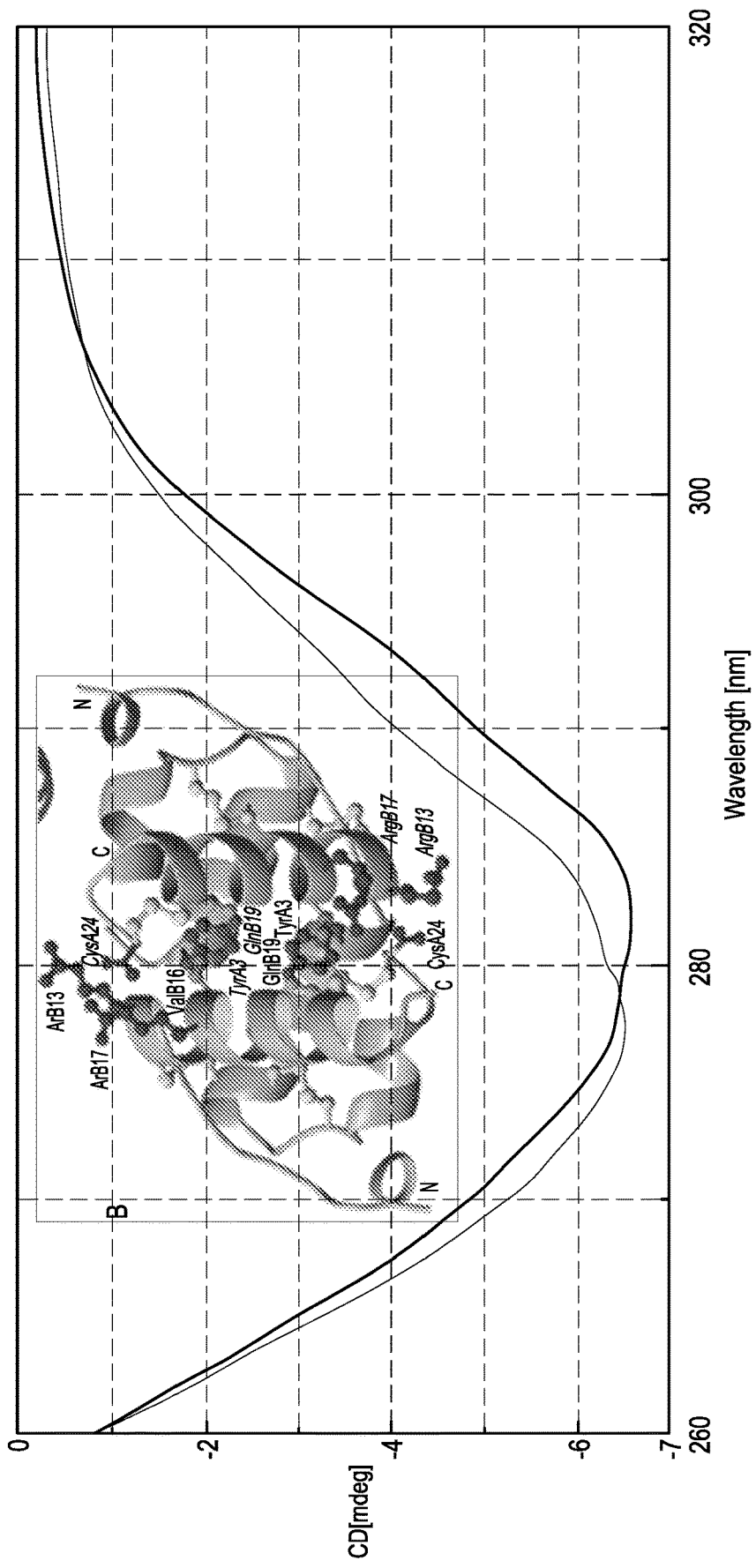
FIG. 26: Near UV CD spectra of Relaxin before (blue) and after the addition of 120 equiv $NH_4Cl$ (blue and green, respectively).

Subtle modifications on the structure of Relaxin found further support on $^{15}$N NMR HSQC spectroscopic studies consistent with protein folding going to higher percentage of random coil upon addition of NH$_4$Cl (FIG. 25) and near UV CD investigations that showed small differences in the fingerprint region of Relaxin's tertiary structure possibly due to dimerization interface changes (FIG. 26).

Example 6

Typical Procedure and Results

Based on the studies reported in this memorandum, the combination of PABH and NH$_4$Cl was recommended for use at larger scale. Results from various protein systems are given in the following table.

TABLE 9

| Protein/PEG-OA | Conditions[1] | Conversion (%) |
|---|---|---|
| Relaxin/20 kDa PEG-OA | 30 equiv PABH, 120 equiv NH$_4$Cl, 20° C. | 94 |
| Relaxin/dPEG36-OA | 30 equiv PABH, 30° C. | 90 |
| FGF21 G1/30 kDa PEG-OA | 30 equiv PABH, 120 equiv NH$_4$Cl, 20° C. | 88 |
| FGF21 G2/30 kDa PEG-OA | 30 equiv PABH, 120 equiv NH$_4$Cl, 20° C. | 98 |

[1]Conditions: 1.2 equiv PEG-OA reagent, 20° C. unless otherwise indicated. Conversions were determined by HPLC assay after 18-24 h reaction time.

One consideration when using PABH in PEGylation reactions is the purity of the commercially available reagents is not equal across vendors. Use of 98% PABH on large scale resulted in an impurity peak co-eluting with the desired product during the chromatography. Isolation of these impurities confirmed their structures to be the hydrazide and amide impurities present in the PABH (FIG. 27).

Due to the high equivalents used in the reaction, even low level impurities in this reagent can have an impact. Thus, it is recommended to pursue the highest quality PABH available.

Example 7

Typical Screening Procedure

The use of the additives is operationally simple. PEGylation of FGF21 G1 with 30 kDa PEG-OA is given as a representative example.

TABLE 10

Reagents and their concentrations

| Items | Amt (mg) | Vol (mL) | MW | μmol |
|---|---|---|---|---|
| FGF21 Solution | 20.3 | 1.0 | 19585 | 1.04 |
| PABH | 4.7 | | 151.17 | 31.2 |
| NH$_4$Cl | 6.7 | | 53.49 | 125 |
| 30 kDa PEG-OA | 39.0 | | 31000 | 1.26 |

Procedure

A solution of FGF21 (1.0 mL, 20.3 mg/mL, 1.04 μmol) in 20 mM NaOAc, 6M urea, with pH 4 was added to solid NH$_4$Cl (6.7 mg, 124.8 μmol) in a clean 1.5 mL vial. The mixture was gently agitated until all the solid dissolved. In a separate vial, MPEG 30 kDa (39.0 mg, 1.26 μmol) and PABH (4.7 mg, 31.2 μmol) were combined. The protein solution from the first vial was transferred to the second vial containing the PEGylating reagent and PABH, and the mixture gently agitated until the solids dissolved (ca 20 min). The pH was measured and the mixture adjusted to pH 4 using 0.1M HCl if needed.

Typical reaction mixture are homogenous solutions, thus the reaction solution was held at 20-25° C. without stirring. Reaction progress is monitored by HPLC either using ELS or UV detection at 280 nm. Reaction completion is assessed by HPLC analysis versus an external standard.

Example 8

Comparison of PEGylation Conditions

The final goal of this initiative was to demonstrate the utility of this new PEGylation procedure versus the procedures in place at the time of the start of the project, as well as the "state of the art" conditions in the literature. This is primarily to quantify the savings in expensive PEGylating reagents available by use of the additive combinations recommended. Table 11 includes the original conditions used for Relaxin and FGF21 G1 PEGylations as well as the PEGylations mediated by the PABH additive.

TABLE 11

Comparison of PEGylation Conditions with Emphasis on Potential Cost Savings

| Protein | PEG | PEG (equiv) | T (° C.) | PABH (equiv) | NH$_4$Cl (equiv) | Conv (%) | Notes |
|---|---|---|---|---|---|---|---|
| Relaxin | 20 kDa PEG-OA | 1.5 | 50 | N/A | N/A | 96 | Original conditions. |

TABLE 11-continued

Comparison of PEGylation Conditions with
Emphasis on Potential Cost Savings

| Protein | PEG | PEG (equiv) | T (° C.) | PABH (equiv) | NH$_4$Cl (equiv) | Conv (%) | Notes |
|---|---|---|---|---|---|---|---|
| Relaxin | 20 kDa PEG-OA | 1.2 | 20 | 30 | 120 | 94 | 20% reduction in PEG with similar yield. |
| FGF21 G1 | 30 kDa PEG-OA | 2.5 | 20 | N/A | N/A | 75 | Original conditions. |
| FGF21 G1 | 30 kDa PEG-OA | 1.2 | 20 | 30 | 120 | 88 | 58% reduction in PEG plus 13% increase in yield. |

Potential reduction in cost for the Relaxin compound is purely related to the amount of the PEG 20 kDa reagent used, as the conversions and yields of both processes is comparable. However, for the PEGylation of the first generation FGF21 asset, the savings is quite dramatic. More than 50% reduction in the PEG loading combined with a 13% increase in reaction yield result in an overall 70% reduction in cost associated with its production. As the cost of PABH and NH$_4$Cl are both extremely low relative to the PEGylating reagents, their use contributes minimally to the overall cost of production. In the following table we compare the PABH conditions with those using acetyl hydrazide.

TABLE 12

Summary of Results of PEGylation of Various Protein Systems and
Comparison with Acetyl Hydrazide

| Protein | Conditions[1] | Conversion (%) |
|---|---|---|
| Relaxin G1 | [2]No additives, 50° C. | 97 |
|  | [2]No additives, 20° C. | 75 |
|  | [2]30 equiv AcNHNH$_2$, no co-additive, 20° C. | 90 |
|  | 30 equiv PABH, no co-additive, 20° C. | 86 |
|  | 30 equiv PABH, 120 equiv NH$_4$Cl, 20° C. | 94 |
| Relaxin G2 | No additives, 40° C. | 70 |
|  | No additives, 30° C. | 70 |
|  | 30 equiv AcNHNH$_2$, no co-additive, 30° C. | 80 |
|  | 30 equiv PABH, no co-additive, 30° C. | 95 |
|  | 30 equiv PABH, NH$_4$Cl, 30° C. | 90 |
| FGF21 G1 | No additives, 20° C. | 53 |
|  | 30 equiv AcNHNH$_2$, no co-additive, 20° C. | 80 |
|  | 30 equiv AcNHNH$_2$, 120 equiv NH$_4$Cl | 82 |
|  | 30 equiv PABH, 120 equiv NH$_4$Cl, 20° C. | 88 |
| FGF21 G2 | 30 equiv PABH, 120 equiv NH$_4$Cl, 20° C. | 98 |

[1]All reactions were run using 1.2 equiv of PEGylating reagent, unstirred at 20° C.
[2]Reactions were run using 1.5 equiv PEGylating reagent.

Some of the advantages of the additive system in the present disclosure are listed below:

1) Promotion of higher conversions with considerably lower amounts of PEGylating reagent (1.2 equiv relative to 1.5-2.5 equiv), which is extremely expensive. The below table provides a comparison that highlights the improvements over the old method (standard conditions).

| Molecule | Standard Conditions | Conversion | Conditions with Additives | Conversion with Additives |
|---|---|---|---|---|
| Relaxin | 1.5 equiv PEG 50° C., 48 h | 96% | 1.2 equiv PEG 60 equiv p-NHBzNHNH$_2$ 120 equiv NH$_4$Cl 20° C., 10 h | 96% |
| FGF21 | 2.5 equiv PEG Urea 6M 20° C., 24 h | 75% | 1.2 equiv PEG 30 equiv p-NHBzNHNH$_2$ 120 equiv NH$_4$Cl 20° C., 24 h | 82% |
| FGF21-GEN2 | 1.6 equiv PEG 30 equiv AcNHNH$_2$ 20° C., 24 h | 88% | 1.2 equiv PEG 60 equiv p-NHBzNHNH$_2$ 120 equiv NH$_4$Cl 20° C., 24 h | 89% |

The combination of two additives greatly increases reaction rate and conversions, and allows for dramatic reduction of PEG loading versus the original conditions.

2) Promotion of faster reactions that circumvent the need for high reaction temperatures. Avoiding high temperatures diminishes associated concerns about protein structural modification and stability in the reaction.

3) Substitution of acetylhydrazide (Ames positive) by PABH (Ames negative in preliminary studies). Eliminates the use of a genotoxic material and associated controls in the final product.

Pharmaceutical Compositions

The PEGylated proteins prepared in accordance with instant disclosure may be further rendered suitable for injection by mixture or combination with an additional pharmaceutically acceptable carrier or vehicle by methods known in the art. Among the pharmaceutically acceptable carriers for formulating the products of the invention are saline, human serum album, human plasma proteins, etc. The invention also relates to pharmaceutical compositions comprising a conjugate as described above and a pharmaceutically acceptable excipient and/or carrier. Such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like. The protein conjugates prepared in accordance with instant disclosure may be formulated in pharmaceutical compositions suitable for injection with a pharmaceutically acceptable carrier or vehicle by methods known in the art. See, e.g., WO 97/09996, WO 97/40850, WO 98/58660, and WO 99/07401 (each of which is hereby incorporated by reference in its entirety).

It will be evident to one skilled in the art that the present disclosure is not limited to the foregoing disclosure and that it can be embodied in other specific forms without departing from the essential attributes thereof. It is therefore desired that the instant disclosure be considered in all respects as illustrative and not restrictive, reference being made to the appended claims, rather than to the foregoing disclosure, and all changes which come within the meaning and range of equivalency of the claims are therefore intended to be embraced therein.

We claim:

1. A process for obtaining PEGylated protein, said process comprising steps of:
    (a) identifying a protein, PEG reagent and an additive system;
    (b) solubilizing the protein followed by combining the protein with the PEG reagent in presence of the additive system,
    (c) reacting the protein with the PEG reagent to form a ketoxime and obtain PEGylated protein,
    wherein said additive system includes p-aminobenzoic hydrazide.

2. The process of claim 1, wherein said protein carries a p-acetylphenylalanine residue.

3. The process of claim 1, wherein the solubilized protein combined with the PEG reagent in presence of the additive system is maintained at a pH of about 4.

4. The process of claim 1, wherein the solubilized protein combined with the PEG reagent in presence of the additive system is held at a temperature ranging from about 20° C. to about 25° C.

5. The process of claim 1, wherein said additive system includes p-aminobenzoic hydrazide in combination with an aromatic amine, such as 3,5-diaminobenzoic acid, or an ammonium salt, such as ammonium acetate or ammonium chloride.

6. The process of claim 5, wherein said additive system further includes ammonium chloride.

7. The process of claim 1, wherein said PEG reagent is selected from a group comprising PEG-OA and other PEG derivatives with an aminoxy group.

8. The process of claim 2, wherein said protein is Relaxin or FGF21.

* * * * *